US012758825B2

(12) United States Patent
Choi et al.

(10) Patent No.: US 12,758,825 B2
(45) Date of Patent: Oct. 13, 2026

(54) ELECTRONIC DEVICE FOR PROVIDING EXERCISE PROGRAM USING MEDICAL DATA AND METHOD THEREFOR

(71) Applicant: SAMSUNG ELECTRONICS CO., LTD., Suwon-si (KR)

(72) Inventors: Hyeeun Choi, Suwon-si (KR); Daesung Cho, Suwon-si (KR); Eunyoung Choi, Suwon-si (KR); Sangsu Nam, Suwon-si (KR); Kyungsub Min, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 119 days.

(21) Appl. No.: 18/370,562

(22) Filed: Sep. 20, 2023

(65) Prior Publication Data

US 2024/0009517 A1 Jan. 11, 2024

Related U.S. Application Data

(63) Continuation of application No. PCT/KR2022/001808, filed on Feb. 7, 2022.

(30) Foreign Application Priority Data

Mar. 24, 2021 (KR) ........................ 10-2021-0037829

(51) Int. Cl.

*A63B 24/00* (2006.01)
*A63B 71/06* (2006.01)
*G16H 20/30* (2018.01)

(52) U.S. Cl.

CPC ...... *A63B 24/0075* (2013.01); *A63B 71/0622* (2013.01); *G16H 20/30* (2018.01);

(Continued)

(58) Field of Classification Search

CPC ............ A63B 24/0075; A63B 71/0622; A63B 2024/0068; A63B 2220/62;

(Continued)

(56) References Cited

U.S. PATENT DOCUMENTS 7,676,262 B1 * 3/2010 Xi ........................ A61B 5/0245 600/509
11,712,603 B1 * 8/2023 Wang .................. A61M 16/024 482/9

(Continued)

FOREIGN PATENT DOCUMENTS

KR 10-2007-0079767 A 8/2007
KR 10-2009-0077419 A 7/2009

(Continued)

OTHER PUBLICATIONS

W. Zhang, C. Su and C. He, "Rehabilitation Exercise Recognition and Evaluation Based on Smart Sensors With Deep Learning Framework," in IEEE Access, vol. 8, pp. 77561-77571, 2020 (Year: 2020).*

(Continued)

*Primary Examiner* — Matthew L Hamilton
(74) *Attorney, Agent, or Firm* — Sughrue Mion, PLLC

(57) ABSTRACT

An electronic device includes: a communication interface configured to receive medical data of a user from a server; at least one processor electrically connected to the communication module; and a memory electrically connected to the at least one processor. The at least one processor is configured to: determine whether the user is in a rehabilitation condition based on the received medical data; when the user is determined to be in the rehabilitation condition, provide an exercise program corresponding to a recovery target part of the user using the received medical data; and provide feedback on the exercise program based on at least one of (Continued)

exercise performance data, biometric information, or an exercise-related recovery level of the user.

19 Claims, 11 Drawing Sheets

(52) U.S. Cl.
CPC ... *A63B 2024/0068* (2013.01); *A63B 2220/62* (2013.01); *A63B 2230/04* (2013.01); *A63B 2230/207* (2013.01); *A63B 2230/62* (2013.01)

(58) Field of Classification Search
CPC .......... A63B 2230/04; A63B 2230/207; A63B 2230/62; G16H 20/30
See application file for complete search history.

(56) References Cited

U.S. PATENT DOCUMENTS

| | | | | |
|---|---|---|---|---|
| 2011/0065549 | A1* | 3/2011 | Jung | A63B 24/0062 482/4 |
| 2011/0294624 | A1* | 12/2011 | Burnfield | A63B 21/00181 482/145 |
| 2013/0209978 | A1* | 8/2013 | Chen | A61B 5/1118 434/247 |
| 2013/0268292 | A1 | 10/2013 | Kim et al. | |
| 2015/0196805 | A1 | 7/2015 | Koduri et al. | |
| 2015/0302766 | A1* | 10/2015 | Oberlander | G06Q 10/10 434/247 |
| 2016/0213979 | A1* | 7/2016 | Lee | G16H 40/63 |
| 2018/0261316 | A1* | 9/2018 | Spooner | A61B 5/681 |
| 2021/0035674 | A1* | 2/2021 | Volosin | G16H 50/70 |
| 2021/0197023 | A1* | 7/2021 | Liang | A63B 24/0087 |
| 2021/0225505 | A1* | 7/2021 | Khare | G06F 11/3089 |
| 2022/0310227 | A1* | 9/2022 | Ogasawara | A61B 5/00 |

FOREIGN PATENT DOCUMENTS

| | | | |
|---|---|---|---|
| KR | 10-2012-0076615 | A | 7/2012 |
| KR | 10-2014-0015678 | A | 2/2014 |
| KR | 10-1490410 | B1 | 2/2015 |
| KR | 10-2016-0044269 | A | 4/2016 |
| KR | 10-2016-0143012 | A | 12/2016 |
| KR | 10-2017-0136297 | A | 12/2017 |
| KR | 10-1948115 | B1 | 2/2019 |
| KR | 10-2094294 | B1 | 3/2020 |

OTHER PUBLICATIONS

Sears, PT, B., "A Walkthrough of Cardiac Rehab Phases 1-4" verywellhealth, (Aug. 15, 2022), 5 pages.
McMahon, S. R., et al., "The role of cardiac rehabilitation in patients with heart disease" Trends Cardiovasc Med. (Aug. 27, 2017), (6): 420-425, 11 pages. doi:10.1016/j.tcm.2017.02.005.
Sukala, B., "Heart Valve Surgery Exercise Guidelines", (Nov. 10, 2019), 19 pages.
"Exercise Prescription", Doctor's Handbook, Centre for Health Protection, (2012), 126 pages, http://exerciserx.cheu.gov.hk.
https://www.hl7.org/fhir/, Release 5, (Mar. 26, 2023), 2 pages.
"Rehabilitation of stroke patients", Korean Academy of Rehabilitation Medicine, 5 pages.
Communication issued Jun. 17, 2024 by the European Patent Office in European Patent Application No. 22775892.7.

* cited by examiner

ELECTRONIC DEVICE FOR PROVIDING EXERCISE PROGRAM USING MEDICAL DATA AND METHOD THEREFOR

CROSS-REFERENCE TO RELATED APPLICATION(S)

This application is a bypass continuation of International Application No. PCT/KR2022/001808, filed on Feb. 7, 2022, which is based on and claims priority to Korean Patent Application No. 10-2021-0037829, filed on Mar. 24, 2021, in the Korean Intellectual Property Office, the disclosures of which are incorporated by reference herein in their entireties.

TECHNICAL FIELD

The disclosed embodiments below relate to an electronic device for providing an exercise program using medical data and a method therefor.

BACKGROUND

Recently, interest in planned exercise for maintaining health and improving physical strength is increasing. In order to maintain health through exercise and recover poor functions of the body, it is desirable to perform the appropriate type of exercise in an appropriate way. Recently, medical institutions provide exercise prescriptions that instruct types and methods of exercise in consideration of, for example, treatment or medication prescriptions, and/or health conditions and physical strength of individuals. When an exercise prescription is presented, it is important to perform the exercise in an appropriate way.

SUMMARY

A conventional exercise program device is configured for a user to directly manually manipulate a program or configured to operate according to preset contents, and thus, there is problems that the exercise program device does not operate by reflecting a current condition change of a user in real time and does not reflect an exercise prescription instructed by a medical institution. An improved electronic device may determine an exercise program based on exercise prescription data recorded in medical data (e.g., personal health record data, electronic medical record data, or electronic health record data), thereby reflecting an exercise prescription instructed by a medical institution. An improved electronic device may measure exercise performance data, biometric information, and an exercise-related recover level of a user, and change an exercise program based on the measured data, thereby providing a user with the exercise program in which a condition change of the user is reflected in real time. The improved electronic device may provide an exercise performance result and exercise performance data to a healthcare provider, thereby providing a user with an exercise program changed based on exercise prescription data newly prescribed by the healthcare provider. Furthermore, the improved electronic device may control an exercise machine to operate according to an exercise program by establishing communication with the exercise machine.

An electronic device may include: a communication interface configured to receive medical data of a user from a server; at least one processor electrically connected to the communication module; and a memory electrically connected to the at least one processor. The at least one processor may be configured to: determine whether the user is in a rehabilitation condition based on the received medical data; when the user is determined to be in the rehabilitation condition, provide an exercise program corresponding to a recovery target part of the user using the received medical data; and provide feedback on the exercise program based on at least one of exercise performance data, biometric information, or an exercise-related recovery level of the user.

The at least one processor being configured to determine whether the user is in a rehabilitation condition may include being configured to: extract treatment information from the received medical data; and in response to determining that a current time point is before an expected recovery time of the user from a treatment start time point has elapsed, determine that the user is in the rehabilitation condition, the expected recovery time of the user being based on the treatment information.

The at least one processor being configured to provide the exercise program corresponding to the recovery target part of the user may include being configured to: in response to exercise prescription data being searched from the received medical data, determine at least one or a combination of two or more of an exercise identification, a target exercise frequency, a target exercise time, or a target exercise intensity of the exercise program based on the searched exercise prescription data; and in response to the exercise prescription data not being searched from the received medical data, determine at least one or a combination of two or more of the exercise identification, the target exercise frequency, the target exercise time, or the target exercise intensity of the exercise program according to the treatment information and the recover level of the user.

The at least one processor may be further configured to: while the user is determined to be in a normal condition, obtain biometric information of the user in a first cycle; and while the user is determined to be in the rehabilitation condition, obtain the biometric information of the user in a second cycle which is shorter than the first cycle.

The at least one processor may be further configured to: while the user is determined to be in a normal condition, determine whether the user is exercising based on a first exercise condition; and while the user is determined to be in the rehabilitation condition, determine whether the user is exercising based on a second exercise condition that is different than the first exercise condition.

The at least one processor being configured to provide the feedback on the exercise program may include being configured to: when the user is determined to be exercising, provide one of change or termination of the exercise program by adjusting an exercise level of the exercise program based on at least one of the exercise performance data or the biometric information of the user during the exercising.

The at least one processor may be further configured to: determine the exercise-related recovery level using at least one or a combination of two or more of an increasing speed of a heart rate (HR) of the user during the exercising, an exercise duration, center of gravity balance information, saturation of percutaneous oxygen (SpO2) information, blood pressure (BP) information, and HR recovery time after the exercising.

The at least one processor being configured to provide the feedback on the exercise program may include being configured to: when the user is exercising, in response to at least one of determining that the exercising performed by the user does not match with an exercise identification of the exercise program, determining that an exercise intensity of the exercising performed by the user exceeds an intensity limit, determining that an exercise duration of the exercising performed by the user exceeds a duration limit, or determining that biometric information sensed for the user exceeds a biometric level limit, output a warning message to a display module.

The communication interface may be further configured to establish communication with an exercise machine. The at least one processor may be further configured to instruct the exercise machine to perform at least one or a combination of two or more of exercise start, exercise intensity control, exercise termination, and warning instruction of the exercise machine based on the exercise program.

The communication interface may be further configured to establish communication with an exercise machine operable according to the exercise program. The at least one processor may be further configured to when the user is determined to be exercising: adjust an exercise level of the exercise program based on at least one of the exercise performance data or the biometric information of the user during the exercising, and transmit, to the exercise machine, an instruction indicating at least one of a decrease in an exercise intensity or exercise termination of the exercise machine.

A method performed by an electronic device may include: determining whether a user is in a rehabilitation condition based on medical data of the user received from a server; when the user is determined to be in the rehabilitation condition, providing an exercise program corresponding to a recovery target part of the user using the received medical data; and providing feedback on the exercise program based on at least one of exercise performance data, biometric information, or an exercise-related recover level of the user.

The determining whether the user is in the rehabilitation condition may include: extracting treatment information from the received medical data; and in response to determining that a current time point is before an expected recovery time of the user from a treatment start time point has elapsed, determining that the user is in the rehabilitation condition, the expected recovery time of the user being based on the treatment information.

The providing the exercise program corresponding to the recovery target part of the user may include: in response to exercise prescription data being searched from the received medical data, determining at least one or a combination of two or more of an exercise identification, a target exercise frequency, a target exercise time, or a target exercise intensity of the exercise program based on the searched exercise prescription data; and in response to the exercise prescription data not being searched from the received medical data, determining at least one or a combination of two or more of the exercise identification, the target exercise frequency, the target exercise time, or the target exercise intensity of the exercise program according to treatment information and the recover level of the user.

The method may further include: while the user is determined to be in a normal condition, obtaining biometric information of the user in a first cycle, and determining whether the user is exercising based on a first exercise condition; and while the user is determined to be in the rehabilitation condition, obtaining the biometric information of the user in a second cycle which is shorter than the first cycle, and determining whether the user is exercising based on a second exercise condition different from the first exercise condition.

The providing the feedback on the exercise program may include: when the user is determined to be exercising, providing one of change or termination of the exercise program by adjusting an exercise level of the exercise program based on at least one of the exercise performance data or the biometric information of the user during the exercising.

The providing the feedback on the exercise program may include: when the user is exercising, in response to at least one of determining that the exercising performed by the user does not match with an exercise identification of the exercise program, determining that an exercise intensity of the exercising performed by the user exceeds an intensity limit, determining that an exercise duration of the exercising performed by the user exceeds a duration limit, or determining that biometric information sensed for the user exceeds a biometric level limit, outputting a warning message to a display module.

The method may further include: while the user is determined to be in a normal condition, determining whether the user is exercising based on a first exercise condition; and while the user is determined to be in the rehabilitation condition, determining whether the user is exercising based on a second exercise condition that is different than the first exercise condition.

The method may further include: determining the exercise-related recovery level using at least one or a combination of two or more of an increasing speed of a heart rate (HR) of the user during the exercising, an exercise duration, center of gravity balance information, saturation of percutaneous oxygen (SpO2) information, blood pressure (BP) information, and HR recovery time after the exercising.

The method may further include: instructing an exercise machine to perform at least one or a combination of two or more of exercise start, exercise intensity control, exercise termination, and warning instruction of the exercise machine based on the exercise program.

The method may further include: adjusting an exercise level of the exercise program based on at least one of the exercise performance data or the biometric information of the user during the exercising, and transmitting, to an exercise machine, an instruction indicating at least one of a decrease in an exercise intensity or exercise termination of the exercise machine.

The electronic device may provide the exercise program corresponding to the recovery target part of the user using the medical data received from the server. The electronic device may provide a suitable exercise program to the user.

The electronic device may provide a more suitable exercise program to the user by changing the exercise program using the biometric information and the exercise performance data when the user is exercising.

The electronic device may receive feedback on a next exercise program through an exercise performance result and exercise performance data of the user for the exercise program.

The electronic device may establish communication with the exercise machine operable according to the exercise program, and control settings of the exercise machine according to the exercise program.

DETAILED DESCRIPTION

Figure 1:
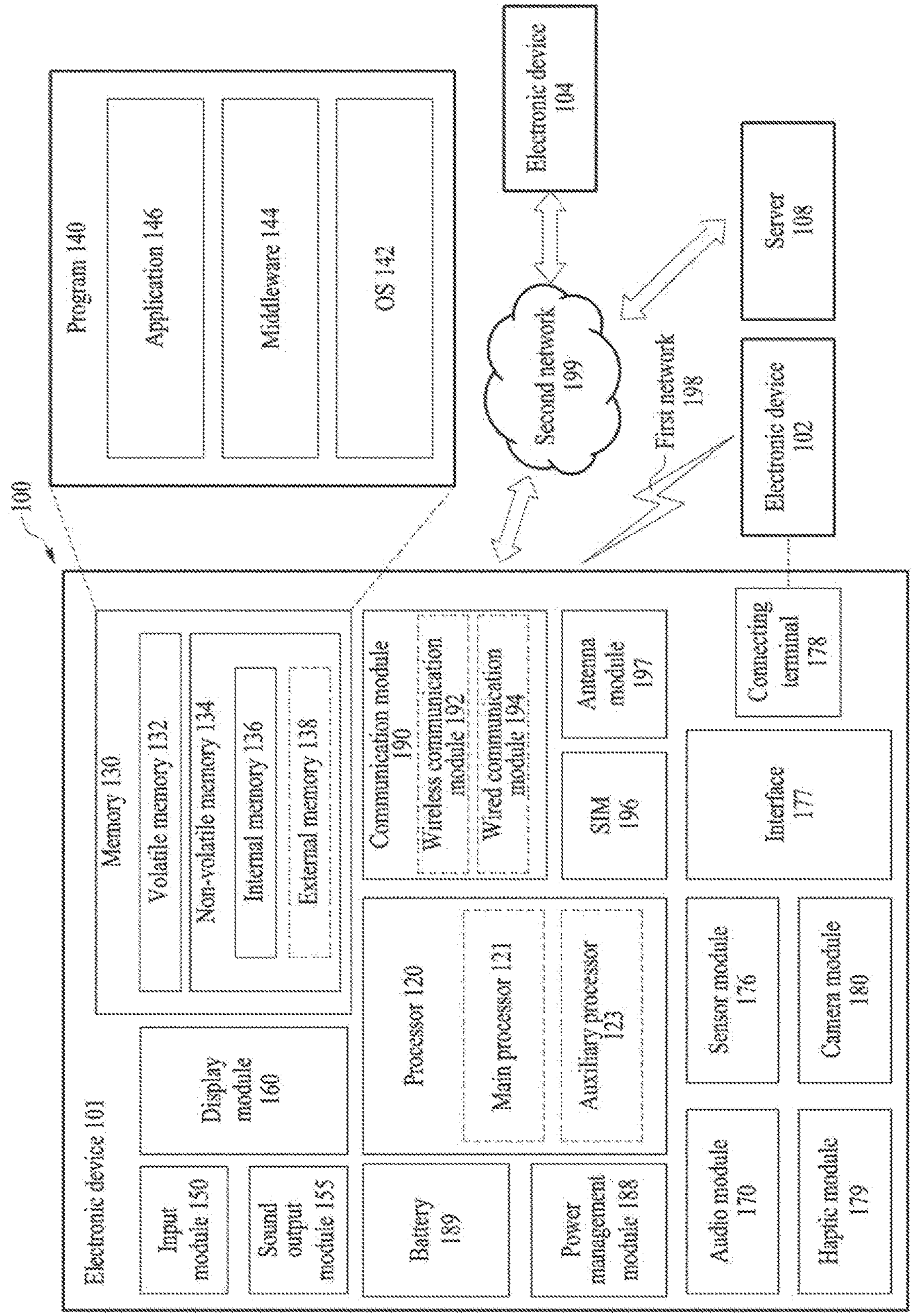
FIG. 1 is a block diagram illustrating an electronic device in a network environment according to various embodiments.

Hereinafter, embodiments will be described in detail with reference to the accompanying drawings. When describing the embodiments with reference to the accompanying drawings, like reference numerals refer to like elements and any repeated description related thereto will be omitted.

FIG. 1 is a block diagram illustrating an electronic device 101 in a network environment 100 according to an embodiment. Referring to FIG. 1, the electronic device 101 in the network environment 100 may communicate with an electronic device 102 via a first network 198 (e.g., a short-range wireless communication network), or communicate with an electronic device 104 or a server 108 via a second network 199 (e.g., a long-range wireless communication network). The electronic device 101 may communicate with the electronic device 104 via the server 108. The electronic device 101 may include a processor 120, a memory 130, an input module 150, a sound output module 155, a display module 160, an audio module 170, and a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be integrated as a single component (e.g., the display module 160).

The processor 120 may execute, for example, software (e.g., a program 140) to control at least one other component (e.g., a hardware or software component) of the electronic device 101 connected to the processor 120, and may perform various data processing or computation. As at least part of data processing or computation, the processor 120 may store a command or data received from another component (e.g., the sensor module 176 or the communication module 190) in a volatile memory 132, process the command or the data stored in the volatile memory 132, and store resulting data in a non-volatile memory 134. The processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently of, or in conjunction with the main processor 121. For example, when the electronic device 101 includes the main processor 121 and the auxiliary processor 123, the auxiliary processor 123 may be adapted to consume less power than the main processor 121 or to be specific to a specified function. The auxiliary processor 123 may be implemented separately from the main processor 121 or as a part of the main processor 121.

The auxiliary processor 123 may control at least some of functions or states related to at least one (e.g., the display module 160, the sensor module 176, or the communication module 190) of the components of the electronic device 101, instead of the main processor 121 while the main processor 121 is in an inactive (e.g., sleep) state or along with the main processor 121 while the main processor 121 is an active state (e.g., executing an application). The auxiliary processor 123 (e.g., an ISP or a CP) may be implemented as a portion of another component (e.g., the camera module 180 or the communication module 190) that is functionally related to the auxiliary processor 123. The auxiliary processor 123 (e.g., an NPU) may include a hardware structure specified for artificial intelligence (AI) model processing. An artificial intelligence model may be generated by machine learning. Such learning may be performed by, for example, the electronic device 101 in which artificial intelligence is performed, or performed via a separate server (e.g., the server 108). Learning algorithms may include, but are not limited to, for example, supervised learning, unsupervised learning, semi-supervised learning, or reinforcement learning. The AI model may include a plurality of artificial neural network layers. An artificial neural network may include, for example, a deep neural network (DNN), a convolutional neural network (CNN), a recurrent neural network (RNN), a restricted Boltzmann machine (RBM), a deep belief network (DBN), and a bidirectional recurrent deep neural network (BRDNN), a deep Q-network, or a combination of two or more thereof, but is not limited thereto. The AI model may additionally or alternatively include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored as software in the memory 130, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output a sound signal to the outside of the electronic device 101. The sound output module 155 may include, for example, a speaker or a receiver. The speaker may be used for general purposes, such as playing multimedia or playing record. The receiver may be used to receive an incoming call. The receiver may be implemented separately from the speaker or as a part of the speaker.

The display module 160 may visually provide information to the outside (e.g., a user) of the electronic device 101. The display module 160 may include, for example, a display, a hologram device, or a projector and control circuitry to control a corresponding one of the display, the hologram device, and the projector. The display module 160 may include a touch sensor adapted to detect a touch, or a pressure sensor adapted to measure the intensity of force incurred by the touch.

The audio module 170 may convert a sound into an electric signal or vice versa. The audio module 170 may obtain the sound via the input module 150, or output the sound via the sound output module 155 or an external electronic device (e.g., the electronic device 102 such as a speaker or a headphone) directly or wirelessly connected to the electronic device 101.

The sensor module 176 may detect an operational state (e.g., power or temperature) of the electronic device 101 or an environmental state (e.g., a state of a user) external to the electronic device 101, and generate an electric signal or data value corresponding to the detected state. The sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., by wire) or wirelessly. The interface 177 may include, for example, a high-definition multimedia interface (HDMI), a universal serial bus (USB) interface, a secure digital (SD) card interface, or an audio interface.

The connecting terminal 178 may include a connector via which the electronic device 101 may be physically connected to an external electronic device (e.g., the electronic device 102). The connecting terminal 178 may include, for example, an HDMI connector, a USB connector, an SD card connector, or an audio connector (e.g., a headphone connector).

The haptic module 179 may convert an electric signal into a mechanical stimulus (e.g., a vibration or a movement) or an electrical stimulus which may be recognized by a user via his or her tactile sensation or kinesthetic sensation. The haptic module 179 may include, for example, a motor, a piezoelectric element, or an electric stimulator.

The camera module 180 may capture a still image and moving images. The camera module 180 may include one or more lenses, image sensors, image signal processors, or flashes.

The power management module 188 may manage power supplied to the electronic device 101. According to an embodiment, the power management module 188 may be implemented as, for example, at least a part of a power management integrated circuit (PMIC).

The battery 189 may supply power to at least one component of the electronic device 101. The battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more CPs that are operable independently of the processor 120 (e.g., an AP) and that support a direct (e.g., wired) communication or a wireless communication. The communication module 190 may include a wireless communication module 192 (e.g., a cellular communication module, a short-range wireless communication module, or a global navigation satellite system (GNSS) communication module) or a wired communication module 194 (e.g., a local area network (LAN) communication module, or a power line communication (PLC) module). A corresponding one of these communication modules may communicate with the external electronic device 104 via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., a LAN or a wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the SIM 196.

The wireless communication module 192 may support a 5G network after a 4G network, and a next-generation communication technology, e.g., a new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., a mmWave band) to achieve, e.g., a high data transmission rate. The wireless communication module 192 may support various technologies for securing performance on a high-frequency band, such as, e.g., beamforming, massive multiple-input and multiple-output (MIMO), full dimensional MIMO (FD-MIMO), an array antenna, analog beam-forming, or a large scale antenna. The wireless communication module 192 may support various requirements specified in the electronic device 101, an external electronic device (e.g., the electronic device 104), or a network system (e.g., the second network 199). The wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. The antenna module 197 may include an antenna including a radiating element including a conductive material or a conductive pattern formed in or on a substrate (e.g., a printed circuit board (PCB)). The antenna module 197 may include a plurality of antennas (e.g., array antennas). In such a case, at least one antenna appropriate for a communication scheme used in a communication network, such as the first network 198 or the second network 199, may be selected by, for example, the communication module 190 from the plurality of antennas. The signal or the power may be transmitted or received between the communication module 190 and the external electronic device via the at least one selected antenna. Another component (e.g., a radio frequency integrated circuit (RFIC)) other than the radiating element may be additionally formed as a part of the antenna module 197.

The antenna module 197 may form a mmWave antenna module. The mmWave antenna module may include a printed circuit board, an RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

Commands or data may be transmitted or received between the electronic device 101 and the external electronic device 104 via the server 108 coupled with the second network 199. Each of the external electronic devices 102 or 104 may be a device of the same type as or a different type from the electronic device 101. All or some of operations to be executed by the electronic device 101 may be executed at one or more external electronic devices (e.g., the external electronic devices 102 and 104, and the server 108). For example, if the electronic device 101 needs to perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and may transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. The external electronic device 104 may include an Internet-of-things (IoT) device. The server 108 may be an intelligent server using machine learning and/or a neural network. The external electronic device 104 or the server 108 may be included in the second network 199. The electronic device 101 may be applied to intelligent services (e.g., smart home, smart city, smart car, or healthcare) based on 5G communication technology or IoT-related technology.

Figure 2A:
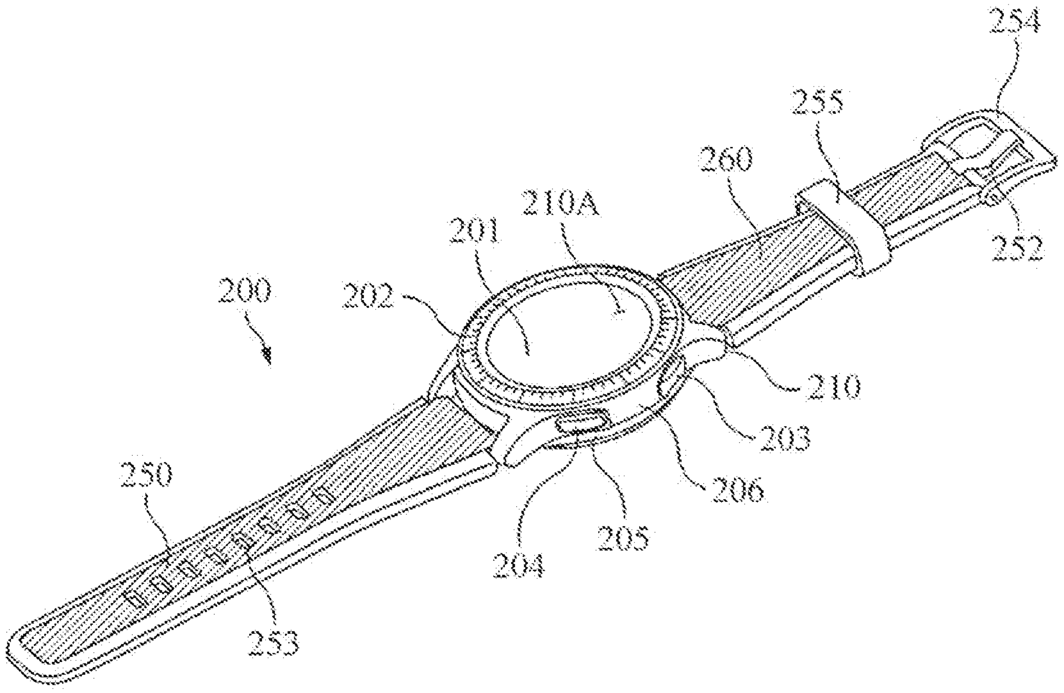
FIGS. 2A and 2B are perspective views of an electronic device according to an embodiment.
Figure 2B:
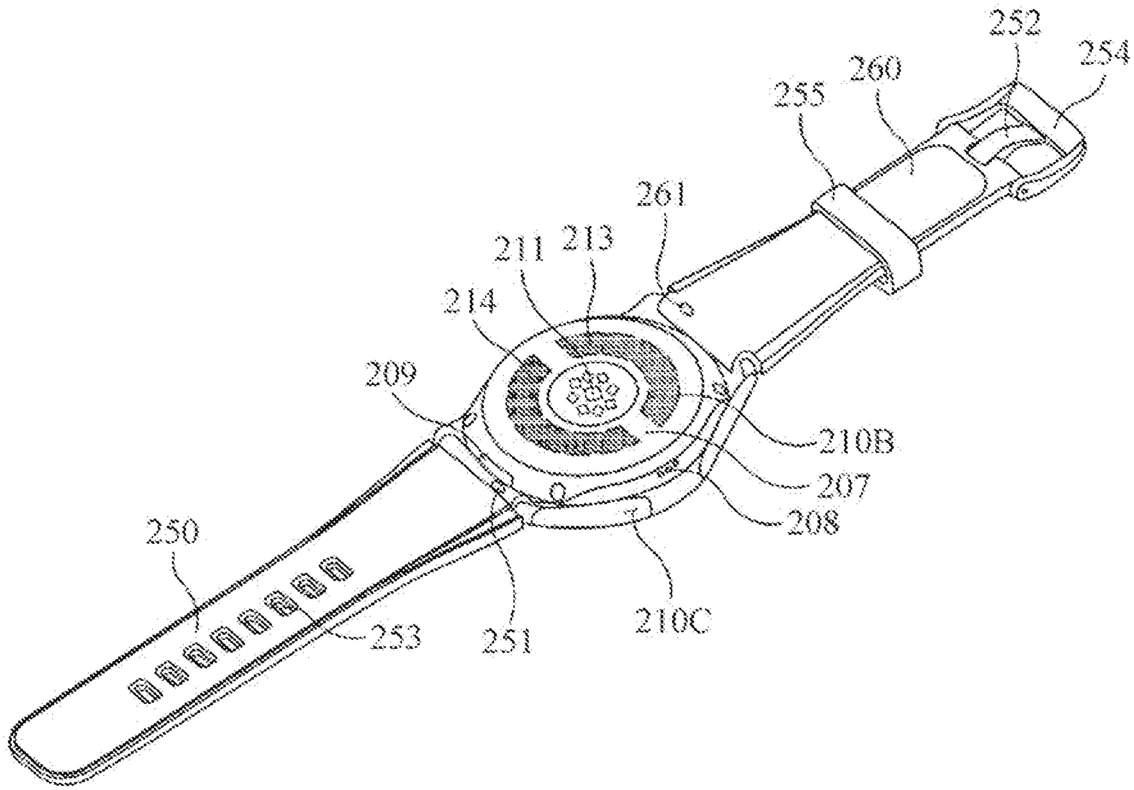

Referring to FIGS. 2A and 2B, An electronic device 200 (e.g., the electronic device 101 of FIG. 1) may include a housing 210 including a first surface (or front surface) 210A, a second surface (or back surface) 210B, and a side surface 210C surrounding a space between the first surface 210A and the second surface 210B, and fastening members 250 and 260 connected to at least a portion of the housing 210 and configured to detachably attach the electronic device 200 to a body part (e.g., wrist or ankle) of a user. According to another embodiment (not shown), a housing may refer to a structure that forms a portion of the first surface 210A, the second surface 210B, and the side surface 210C of FIGS. 2A and 2B. The first surface 210A may be formed of a front plate 201 (e.g., a glass plate or a polymer plate including various coating layers) of which at least a portion is substantially transparent. The second surface 210B may be formed by a rear plate 207 that is substantially opaque. The rear plate 207 may be formed of, for example, coated or colored glass, ceramic, polymer, metal (e.g., aluminum, stainless steel (SS), or magnesium), or a combination of at least two thereof. The side surface 210C may be coupled to the front plate 201 and the rear plate 207 and may be formed by a side bezel structure (or a "side member") 206 including a metal and/or a polymer. The rear plate 207 and the side bezel structure 206 may be integrally formed and may include the same material (e.g., a metal material such as aluminum). The fastening members 250 and 260 may be formed of various materials and may have various shapes. For example, the fastening members 250 and 260 may be formed of woven fabric, leather, rubber, urethane, metal, ceramic, or a combination of at least two of the aforementioned materials and may be implemented in an integrated form or with a plurality of unit links that are movable relative to each other.

The electronic device 200 may include at least one of a display 220, audio modules 205 and 208, a sensor module 211, key input devices 202, 203, and 204, and a connector hole 209. The electronic device 200 may not include at least one (e.g., the key input devices 202, 203, and 204, the connector hole 209, or the sensor module 211) of the components, or additionally include other components.

The display 220 may be visually exposed through a substantial portion of the front plate 201, for example. The display 220 may be provided in a shape corresponding to a shape of the front plate 201, which may be various shapes such as a circle, an ellipse, or a polygon. The display 220 may be coupled to or disposed adjacent to a touch sensing circuit, a pressure sensor configured to measure the intensity (pressure) of a touch, and/or a fingerprint sensor.

The audio modules 205 and 208 may include a microphone hole 205 and a speaker hole 208. A microphone for acquiring an external sound may be disposed in the microphone hole 205. In some embodiments, a plurality of microphones may be disposed to detect a direction of a sound. The speaker hole 208 may be used as an external speaker and a call receiver for calls. The speaker hole 208 and the microphone hole 205 may be implemented as a single hole, or a speaker (e.g., a piezo speaker) may be included without the speaker hole 208.

The sensor module 211 may generate an electrical signal or a data value corresponding to an internal operating state of the electronic device 200 or an external environmental state. The sensor module 211 may include, for example, a biosensor module 211 (e.g., an HRM sensor) disposed on the second surface 210B of the housing 210. The electronic device 200 may further include at least one of sensor modules (not shown), for example, a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The sensor module 211 may include electrode areas 213 and 214 that form a portion of the surface of the electronic device 200 and a biosignal detection circuit (not shown) electrically connected to the electrode areas 213 and 214.

For example, the electrode areas 213 and 214 may include a first electrode area 213 and a second electrode area 214 disposed on the second surface 210B of the housing 210. The sensor module 211 may be configured such that the electrode areas 213 and 214 obtain an electrical signal from a body part of the user, and the biosignal detection circuit detects biometric information of the user based on the electrical signal.

The key input devices 202, 203, and 204 may include a wheel key 202 disposed on the first surface 210A of the housing 210 and rotatable in at least one direction, and/or side key buttons 203 and 204 disposed on the side surface 210C of the housing 210. The wheel key 202 may have a shape corresponding to the shape of the front plate 201. According to another embodiment, the electronic device 200 may not include some or all of the key input devices 202, 203, 204, and the key input devices 202, 203, and 204 that are not included may be implemented in other forms such as soft keys on the display 220. The connector hole 209 may include another connector hole (not shown) that accommodates a connector (e.g., a universal serial bus (USB) connector) for transmitting and receiving power and/or data to and from an external electronic device and accommodates a connector for transmitting and receiving an audio signal to and from an external electronic device. The electronic device 200 may further include, for example, a connector cover (not shown) that covers at least a portion of the connector hole 209 and blocks infiltration of external foreign materials into the connector hole 209.

The fastening members 250 and 260 may be detachably fastened to at least a partial area of the housing 210 using locking members 251 and 261. The fastening members 250 and 260 may include one or more of a fixing member 252, a fixing member fastening hole 253, a band guide member 254, and a band fixing ring 255.

The fixing member 252 may be configured to fix the housing 210 and the fastening members 250 and 260 to a part (e.g., a wrist or an ankle) of the user's body. The fixing member fastening hole 253 may correspond to the fixing member 252 to fix the housing 210 and the fastening members 250 and 260 to the part of the user's body. The band guide member 254 may be configured to limit a range of a movement of the fixing member 252 when the fixing member 252 is fastened to the fixing member fastening hole 253, so that the fastening members 250 and 260 may be fastened to the part of the user's body in a state of being brought into close contact with the part of the user's body. The band fixing ring 255 may limit a range of a movement of the fastening members 250 and 260 while the fixing member 252 and the fixing member fastening hole 253 are fastened with each other.

Figure 3:
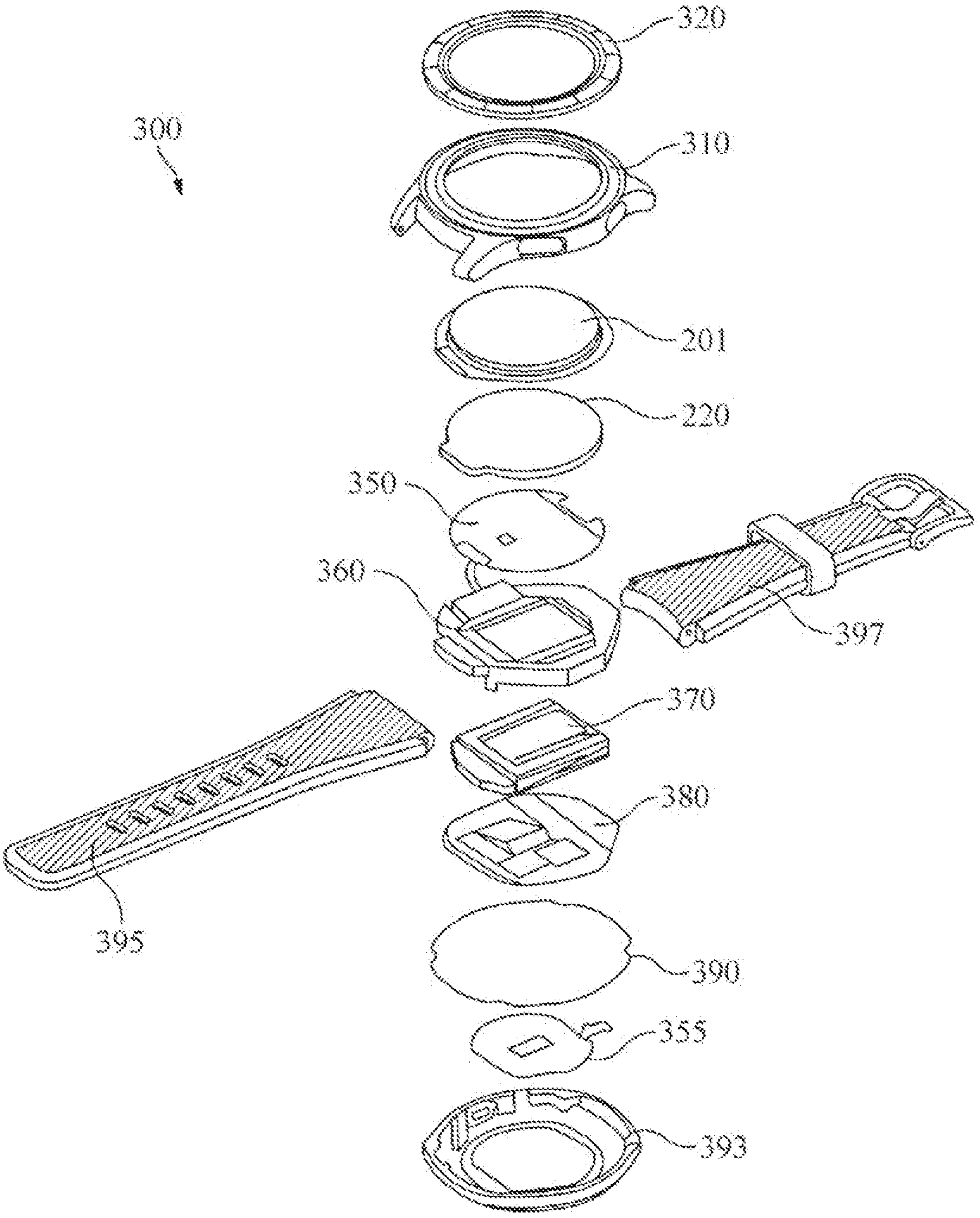
FIG. 3 is an exploded perspective view of an electronic device according to an embodiment.

Referring to FIG. 3, an electronic device 300 (e.g., the electronic device 101 of FIG. 1 or the electronic device 200 of FIG. 2) may include a side bezel structure 310, a wheel key 320, a front plate 201, a display 220, a first antenna 350, a second antenna 355, a support member 360 (e.g., a bracket), a battery 370, a printed circuit board (PCB) 380, a sealing member 390, a back plate 393, and fastening members 395 and 397. At least one of the components of the electronic device 300 may be the same as or similar to at least one of the components of the electronic device 101 of FIG. 1 or the electronic device 200 of FIG. 2, and thus a repeated description thereof will be omitted here. The support member 360 may be disposed inside the electronic device 300 and connected to the side bezel structure 310, or be integrally formed with the side bezel structure 310. The support member 360 may be formed of, for example, a metal material and/or anon-metal material (e.g., polymer). The display 220 may be connected to one surface of the support member 360, and the PCB 380 may be connected to another surface of the support member 360. The PCB 380 may be provided with a processor, a memory, and/or an interface. The processor may include, for example, one or more of a central processing unit (CPU), a graphic processing unit (GPU), an application processor, a sensor processor, or a communication processor.

The memory may include, for example, a volatile memory or a non-volatile memory. The interface may include, for example, a high-definition multimedia interface (HDMI), a USB interface, a secure digital (SD) card interface, or an audio interface. The interface may include, for example, a USB connector, an SD card/multimedia connect (MMC) connector, or an audio connector, to connect, electrically or physically, the electronic device 300 to an external electronic device.

The battery 370, which is a device for supplying power to at least one component of the electronic device 300, may include, for example, a non-rechargeable primary battery, a rechargeable secondary battery, or a fuel cell. For example, at least a portion of the battery 370 may be disposed on substantially the same plane as the PCB 380. The battery 370 may be disposed integrally inside the electronic device 300, or disposed detachably from the electronic device 300.

The first antenna 350 may be disposed between the display 220 and the support member 360. The first antenna 350 may include, for example, a near-field communication (NFC) antenna, a wireless charging antenna, and/or a magnetic secure transmission (MST) antenna. For example, the first antenna 350 may perform short-range communication with an external device, wirelessly transmit and receive power used for charging, or transmit a magnetism-based signal including a short-range communication signal or payment data. An antenna structure may be formed by a portion of the side bezel structure 310 and/or the support member 360, or a combination thereof.

The second antenna 355 may be disposed between the PCB 380 and the rear plate 393. The second antenna 355 may include, for example, an NFC antenna, a wireless charging antenna, and/or an MST antenna. For example, the second antenna 355 may perform short-range communication with an external device, wirelessly transmit and receive power used for charging, or transmit a magnetism-based signal including a short-range communication signal or payment data. An antenna structure may be formed by a portion of the side bezel structure 310 and/or the rear plate 393, or a combination thereof.

The sealing member 390 may be disposed between the side bezel structure 310 and the rear plate 393. The sealing member 390 may be configured to prevent moisture and foreign materials from being introduced into a space surrounded by the side bezel structure 310 and the rear plate 393 from the outside.

The electronic device may be one of various types of electronic devices. The electronic device may include, for example, a portable communication device (e.g., a smartphone), a computer device, a portable multimedia device, a portable medical device, a camera, a wearable device, or a home appliance device. The electronic device is not limited to those described above.

It should be appreciated that disclosed embodiments and the terms used therein are not intended to limit the technological features set forth herein to particular embodiments and include various changes, equivalents, or replacements for a corresponding embodiment. In connection with the description of the drawings, like reference numerals may be used for similar or related components. It is to be understood that a singular form of a noun corresponding to an item may include one or more of the things, unless the relevant context clearly indicates otherwise. As used herein, "A or B," "at least one of A and B," "at least one of A or B," "A, B or C," "at least one of A, B and C," and "at least one of A, B, or C," may include any one of the items listed together in the corresponding one of the phrases, or all possible combinations thereof. Terms such as "$1^{st}$," and "$2^{nd}$," or "first" or "second" may simply be used to distinguish the component from other components in question, and do not limit the components in other aspects (e.g., importance or order). It is to be understood that if an element (e.g., a first element) is referred to, with or without the term "operatively" or "communicatively," as "coupled with," "coupled to," "connected with," or "connected to" another element (e.g., a second element), it means that the element may be coupled with the other element directly (e.g., by wire), wirelessly, or via a third element.

As used in connection with various embodiments, the term "module" may include a unit implemented in hardware, software, or firmware, and may interchangeably be used with other terms, for example, "logic", "logic block", "part", or "circuitry". A module may be a single integral component, or a minimum unit or part thereof, adapted to perform one or more functions. For example, the module may be implemented in a form of an application-specific integrated circuit (ASIC).

Various embodiments as set forth herein may be implemented as software (e.g., the program 140) including one or more instructions that are stored in a storage medium (e.g., the internal memory 136 or an external memory 138) that is readable by a machine (e.g., the electronic device 101). For example, a processor (e.g., the processor 120) of the machine (e.g., the electronic device 101) may invoke at least one of the one or more instructions stored in the storage medium and execute it. This allows the machine to be operated to perform at least one function according to the at least one instruction invoked. The one or more instructions may include code generated by a compiler or code executable by an interpreter. The machine-readable storage medium may be provided in the form of a non-transitory storage medium. The term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

A method disclosed herein may be included and provided in a computer program product. The computer program product may be traded as a product between a seller and a buyer. The computer program product may be distributed in the form of a machine-readable storage medium (e.g., compact disc read-only memory (CD-ROM)), or be distributed (e.g., downloaded or uploaded) online via an application store (e.g., PlayStore™), or between two user devices (e.g., smartphones) directly. If distributed online, at least part of the computer program product may be temporarily generated or at least temporarily stored in the machine-readable storage medium, such as memory of the manufacturer's server, a server of the application store, or a relay server.

According to embodiments, each component (e.g., a module or a program) of the above-described components may include a single entity or multiple entities, and some of the multiple entities may be separately disposed in different components. According to embodiments, one or more of the above-described components or operations may be omitted, or one or more other components or operations may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. According to embodiments, operations performed by the module, the program, or another component may be carried out sequentially, in parallel, repeatedly, or heuristically, or one or more of the operations may be executed in a different order or omitted, or one or more other operations may be added.

An electronic device disclosed in this document is not limited to the form shown in FIGS. 2A to 3. For example, the electronic device may include a wearable electronic device that is wearable on a user, such as a smart ring or smart glasses.

Figure 4:
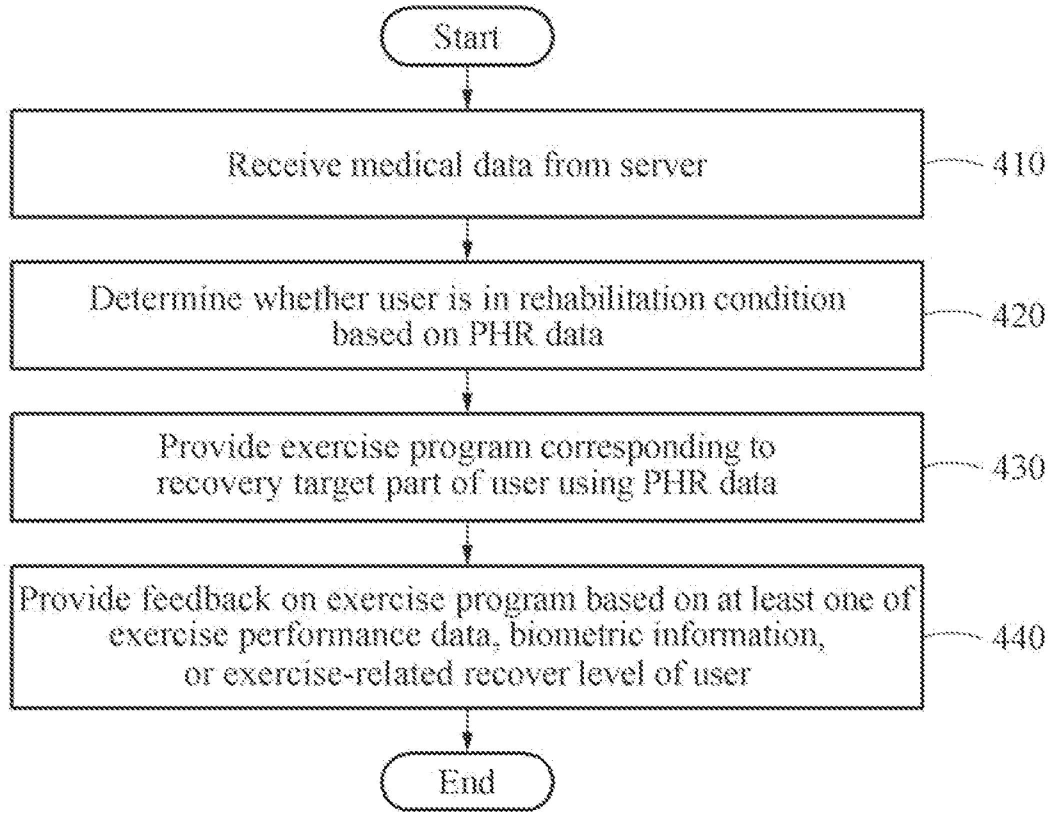
FIG. 4 is a flowchart illustrating an operation of an electronic device according to an embodiment.

FIG. 4 is a flowchart illustrating an operation of an electronic device according to an embodiment.

In operation 410, a communication module (e.g., the communication module 190 of FIG. 1) of an electronic device (e.g., the electronic device 101 of FIG. 1, the electronic device 200 of FIG. 2, or the electronic device 300 of FIG. 3) may receive medical data from a server. Medical data may include data representing conditions related to individual's health, diseases, and treatment. Medical data may include, for example, one or a combination of two or more of personal health record (PHR) data, electronic medical record (EMR) data, or electronic health record (EHR) data. Hereinafter, as an example of the medical data, PHR data will be mainly described, but the medical data is not limited thereto. The PHR data may be transmitted to a server using Fast Healthcare Interoperability Resources (FHIR), a standard framework utilized for healthcare services. The FHIR may include various resources such as Condition, DiagnosticReport, Observation, Procedure, ServiceRequest, and Medication. The electronic device may determine whether a user is in a rehabilitation condition using the FHIR resources included in the PHR data, and provide a suitable exercise program corresponding to a recovery target part of the user. However, as described above, the medical data received by the electronic device may be EMR or EHR, and the electronic device may determine whether the user is in the rehabilitation condition using the EMR data and the EHR data, and provide a suitable exercise program corresponding to the recovery target part of the user.

In operation 420, the electronic device may determine whether the user is in the rehabilitation condition based on the PHR data received from the server. The rehabilitation condition may indicate a condition of a user who needs recovery. The rehabilitation condition may indicate a health condition of a user after the user receives treatment and before a recovery time elapses. A normal condition may indicate a condition of the user who does not need recovery. The normal condition may indicate a health condition of the user after the user receives treatment and the recovery time elapses. The recovery time may be the time required until a patient recovers to a normal condition from the time of surgery or the time of injury.

In operation 430, when the user is in the rehabilitation condition, the electronic device may provide an exercise program corresponding to the recovery target part of the user using the received PHR data. The recovery target part may be a part of the user's body requiring recovery and/or rehabilitation, and may indicate a part of the user's body on which surgery or treatment has been performed. For example, in response to detecting a heart valve replacement surgery record for a user based on the PHR data, the electronic device may determine the heart as the recovery target part of the user. The electronic device may provide an exercise program corresponding to the heart that is suitable for the user. In another example, in response to detecting a treatment record of a stretched ankle ligament of the user based on the PHR data, the electronic device may determine the ankle as the recovery target part of the user. In operation 440, the electronic device may provide feedback on an exercise program based on at least one of exercise performance data, biometric information (biometric data), or an exercise-related recover level of the user. The exercise performance data may indicate data related to a result obtained as the user performs the exercise program provided by the electronic device (e.g., a progress rate of the exercise program, a total exercise time, or biometric information during the exercise).

Biometric information is information indicating a biometric condition of the user, and may include, for example, electrocardiogram (ECG), a blood pressure (BP), saturation of percutaneous oxygen (SpO2), or a heart rate (HR), and may include information related to the user's health. The information related to the user's health may include a stride or center of gravity balance of the user during the exercise.

The exercise-related recover level (hereinafter, a "recover level") may indicate a level of recovery after the surgery or treatment of the user. The recover level may be calculated based on an increasing speed of an HR of the user during the exercise, an exercise time, a change in center of gravity balance, or a change in stride. For example, when the user performs the exercise at the same exercise intensity as a previous exercise, the recover level may be calculated by comparing an increasing speed of the HR during the previous exercise with an increasing speed of the HR during the current exercise. In another example, when the user performs the exercise at the same exercise intensity as the previous exercise, the recover level may be calculated by comparing the exercise time of the previous exercise with the exercise time of the current exercise. In still another example, the recover level may also be calculated by comparing the stride and the center of gravity balance information when the user is in the normal condition with the stride and the center of gravity balance information when the user is in the rehabilitation condition. In addition, the recover level may also be calculated using other biometric information of the user during the exercise (e.g., oxygen saturation information, blood pressure information, and HR recovery time after the exercise), and a method of calculating the recover level will be described in detail with reference to FIG. 8.

A sensor module (e.g., the sensor module 176 of FIG. 1 or the sensor module 211 of FIG. 2) of the electronic device may include a light emitting diode (LED) driver, an LED element, a photodiode (PD), and an analog-to-digital converter (ADC). The sensor module of the electronic device may operate the LED element using the LED driver. The sensor module of the electronic device may emit an optical signal to a body part of the user using the LED driver, and the photodiode may accumulate photocharges corresponding to an amount of reflected or transmitted incident light, and transmit a biosignal in the form of an analog current according to the accumulated photocharges to the ADC. The ADC may convert the biosignal in the form of an analog current into a digital signal. The sensor module of the electronic device may include LED elements having various wavelengths. For example, the sensor module may output, sequentially or at the same time, at least one of a plurality of LEDs which emit light corresponding to each of a red wavelength (600 nanometers (nm) to 700 nm), a green wavelength (500 nm to 600 nm), a blue wavelength (400 nm to 500 nm), or an IR wavelength (780 nm to 1000 nm). A green LED may be most often used to measure the HR of the user. An optical signal emitted by the green LED may have an advantage of being resistant to noise by being shallowly penetrated into the user's skin. A red LED may be used to measure the HR of the user, and an optical signal emitted by the red LED has an advantage of measuring a more accurate HR by being relatively deeply penetrated into the user's skin. An IR LED may be used to measure the HR and the SpO2 of the user. In addition, a blood sugar level of the user may be measured using a blue LED.

According to another embodiment, the sensor module of the electronic device may include an electrode and an ADC. The electrode may be in direct contact with the user's skin. For example, the electrode in contact with the skin may be used to sense or measure an electrical resistance or electrical conductivity. The electrode may be used to sense or detect a voltage corresponding to the electrical resistance or a voltage corresponding to the electrical conductivity. The electrode may measure an analog biosignal (e.g., a bioelectrical impedance analysis (BIA) signal or an electrocardiogram (ECG) signal), and transmit the measured analog signal to the ADC. The sensor module may operate to obtain a plurality of pieces of biometric information, for example, at least two or more pieces of biometric information among the HR, the SpO2, the BIA signal, the ECG signal, or the blood pressure. For example, the sensor module may operate to simultaneously obtain the HR, the SpO2, and the BIA signal.

The sensor module of the electronic device may include a laser diode (LD) and an image sensor.

In addition, in order to obtain the biometric information of the user, the electronic device may include an acceleration sensor, a proximity sensor, a gyro sensor, a temperature sensor, an iris sensor, a temperature-humidity sensor, a pressure sensor, a photoresistor, a time of flight (TOF) sensor, and an ultra-wideband (UWB) sensor. The electronic device may measure the stride of the user using the acceleration sensor and the gyro sensor, and measure the center of gravity balance of the user using the pressure sensor.

Figure 5:
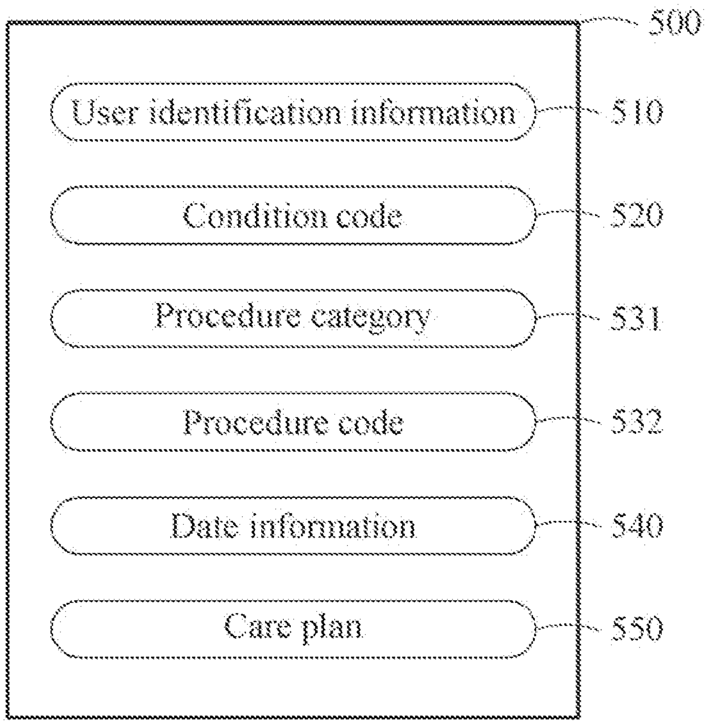
FIG. 5 illustrates fast healthcare interoperability resources (FHIR) of personal health record (PHR) data received by an electronic device from a server according to an embodiment.

FIG. 5 illustrates FHIR of PHR data received by an electronic device from a server according to an embodiment.

The electronic device may receive PHR data from a server. The PHR data may include various FHIR resources. The FHIR resources may include resources corresponding to user identification information 510, a condition code 520, a procedure category 531, a procedure code 532, date information 540, and a care plan 550.

The user identification information 510 may indicate a code or an identification (ID) for identifying a user of the PHR data.

The condition code 520 may be a code indicating a disease that the identified user has. For example, a condition code "928000" may indicate a "musculoskeletal disorder", a condition code "1261007" may indicate "multiple rib fracture", and a condition code "1734006" may indicate a spinal fracture due to a spinal injury.

The procedure category 531 may indicate the type of treatment the user receives. For example, a procedure category "24642003" may indicate a "psychiatric procedure or service", a procedure category "409073007" may indicate "education", and a procedure category "387713003" may indicate a "surgical procedure".

The procedure code 532 may indicate the specific type of the treatment the user receives. For example, a procedure code "34068001" may indicate "heart valve replacement", a procedure code "16521006" may indicate "spinal transplant", and a procedure code "17679005" may indicate "cardiovascular implantation".

The date information 540 may indicate the time when the user receives treatment. In the date information, the time when the treatment is started and the time when the treatment is finished may be recorded.

The care plan 550 may indicate exercise plan information for the user's health recovery. The care plan 550 may include exercise prescription data. The exercise prescription data may indicate an exercise plan prescribed by a healthcare provider for a user who has received the treatment. The electronic device may provide an exercise program corresponding to recovery target part of the user based on the exercise prescription data included in the care plan 550. The electronic device may determine at least one or a combination of two or more of a type of exercise, a target exercise frequency, a target exercise time, or a target exercise intensity of the exercise program based on the exercise prescription data.

Figure 6:
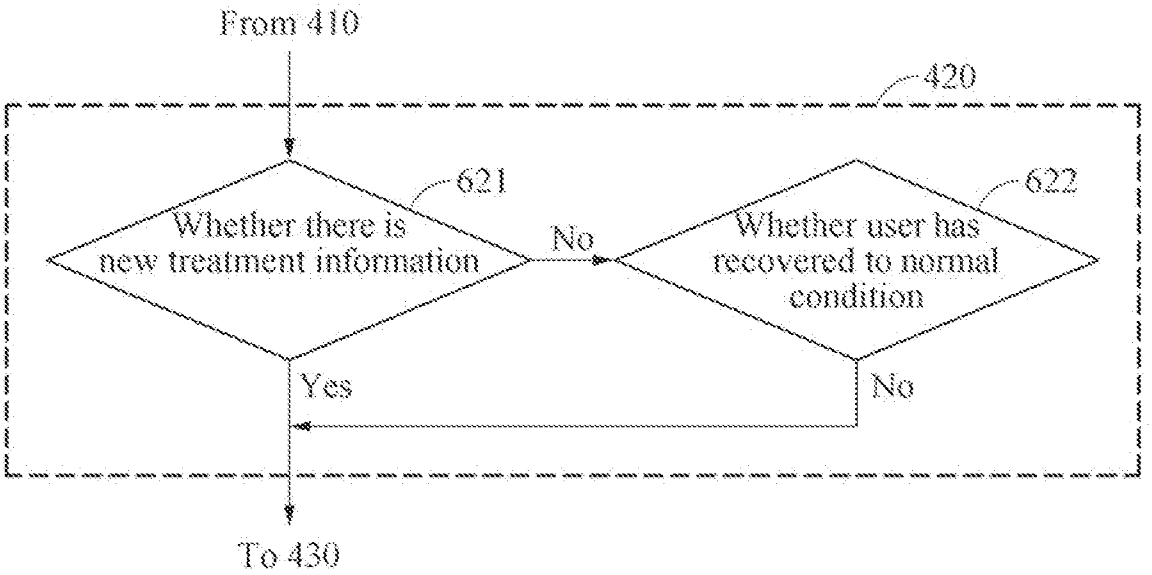
FIG. 6 illustrates a method for an electronic device to determine whether a user is in a rehabilitation condition according to an embodiment.

FIG. 6 illustrates a method for an electronic device to determine whether a user is in a rehabilitation condition according to an embodiment.

The electronic device (e.g., the electronic device 101 of FIG. 1 or the electronic device 200 of FIG. 2) may determine whether the user is in a rehabilitation condition based on the PHR data received from a server.

In operation 621, the electronic device may determine whether there is new treatment information in the PHR data. The treatment information may indicate information related to the treatment the user has received, and may include information on the type of treatment, the specific type of the treatment, the date when the treatment is performed, and the date when the treatment is finished. The electronic device may compare the PHR data received from the server with previous PHR data, and when there is new treatment information, the electronic device may determine whether the user is in the rehabilitation condition using the new treatment information. The new treatment information may indicate treatment information which is not recorded in previous PHR data but is newly added in current PHR data for the user.

The electronic device may extract the newly added treatment information from the PHR data. The electronic device may determine that the user is in the rehabilitation condition in response to a case where a current time point is before an expected recovery time corresponding to the treatment information has elapsed from a treatment start time point. The electronic device may determine whether the user is in the rehabilitation condition using the expected recovery time inferred from existing statistics on the type and the specific type of the treatment. The existing statistics may represent statistics on the record of time taken for people who received the same treatment to recover to the normal condition. For example, when it is confirmed that the user has undergone the heart valve replacement surgery during the surgical procedure based on the PHR data, the electronic device may determine whether the user is in the rehabilitation condition using the expected recovery time (e.g., 100 days) inferred from the existing statistics on the heart valve replacement surgery. When 100 days has not elapsed from the start of the heart valve replacement surgery, the electronic device may determine that the user is in the rehabilitation condition.

In operation 622, the electronic device may compare the current PHR data received from the server with the previous PHR data, and when there is no new treatment information, the electronic device may determine whether the user has recovered to the normal condition. In response to determining that the user has not recovered to the normal condition, the electronic device may determine that the user is still in the rehabilitation condition. For example, the electronic device may measure a biosignal of the user using a sensor module (e.g., the sensor module 176 of FIG. 1 or the sensor module 211 of FIG. 2), and obtain biometric information by processing the biosignal. In response to a significant difference occurring in comparison between the obtained biometric information and pre-stored biometric information, the electronic device may determine that the user has not yet recovered to the normal condition and thus is in the rehabilitation condition. The pre-stored biometric information may be biometric information obtained when the user is in the normal condition.

While the user is in the rehabilitation condition, the electronic device may differently provide a configuration (e.g., a screen configuration or menu configuration) of a guide user interface (UI) to be provided to the user on a display (e.g., the display 220 of FIG. 3) of the electronic device by comparing with the normal condition. While the user is in the rehabilitation condition, the electronic device may configure a screen mainly with a UI related to the exercise so that the user may focus more on the exercise.

The electronic device may further strengthen monitoring of the biometric information of the user while the user is in the rehabilitation condition. While the user is in the rehabilitation condition, the electronic device may increase a measurement frequency of the biosignal compared to the normal condition. While the user is in the normal condition, the electronic device may measure the biosignal of the user in a first cycle. The electronic device may obtain the biometric information in the first cycle by processing the measured biosignal. In contrast, while the user is in the rehabilitation condition, the electronic device may measure the biosignal of the user in a second cycle which is shorter than the first cycle. The electronic device may obtain the biometric information of the user in the second cycle by processing the measured biosignal. While the user is in the rehabilitation condition, the electronic device may set the obtaining cycle of the biometric information to the second cycle which is shorter than the first cycle, in order to more accurately identify a change of the health condition of the user.

While the user is in the rehabilitation condition, the electronic device may increase a measurement intensity of the biosignal or increase the type or number of sensors used for the measurement, compared to the normal condition. While the user is in the normal condition, the electronic device may measure the biosignal of the user with a first intensity. In contrast, while the user is in the rehabilitation condition, the electronic device may measure the biosignal of the user with a second intensity which is greater than or equal to the first intensity. While the user is in the normal condition, the electronic device may measure the biosignal of the user with N sensors in the sensor module. In contrast, while the user is in the rehabilitation condition, in order to more accurately identify the change of the health condition of the user, the electronic device may measure the biometric information with M sensors which are more than the N sensors, or may further activate other types of sensors which are inactivated. For example, while the user is in the rehabilitation condition, the electronic device may increase the number of motion sensors for the measurement, compared to a case where the user is in the normal condition. In another example, a gyro sensor may be activated only when it is necessary while the user is in the normal condition, whereas the electronic device may always activate the gyro sensor to more accurately detect the change of the condition of the user, while the user is in the rehabilitation condition.

While the user is in the rehabilitation condition, the electronic device may flexibly change a method of monitoring the biometric information of the user (e.g., the type of the sensor to be activated, and a time interval and intensity for measurement of a biosignal) according to the type of the exercise of the exercise program provided to the user.

While the user is in the rehabilitation condition, the electronic device may determine whether the user is exercising based on a more relaxed exercise condition compared to the normal condition. While the user is in the normal condition, the electronic device may determine whether the user is exercising based on a first exercise condition. The exercise condition is a condition for determining whether the user is exercising and may be a condition related to biometric information or exercise information of the user. While the user is in the rehabilitation condition, the electronic device may determine whether the user is exercising based on a second exercise condition which is different from the first exercise condition. The second exercise condition may be a more relaxed exercise condition than the first exercise condition.

In a case of the user in the rehabilitation condition, it may be difficult to exercise smoothly compared to a user in the normal condition. Accordingly, when the user is in the rehabilitation condition, the electronic device may determine whether the user is exercising based on the relaxed exercise condition, thereby accurately determining whether the user is exercising. For example, it is assumed that the electronic device determines whether the user is exercising (e.g., walking) based on a minimum exercise time and an average exercise speed of the user. While the user is in the normal condition, the electronic device may determine that the user is walking when the first exercise condition corresponding to a minimum exercise time of 10 minutes or more and an average exercise speed of 5 km/h or more is satisfied. On the other hand, while the user is in the rehabilitation condition, the electronic device may determine that the user is walking when the relaxed second exercise condition corresponding to the minimum exercise time of 5 minutes or more and the average exercise speed of 3 km/h or more is satisfied.

Figure 7A:
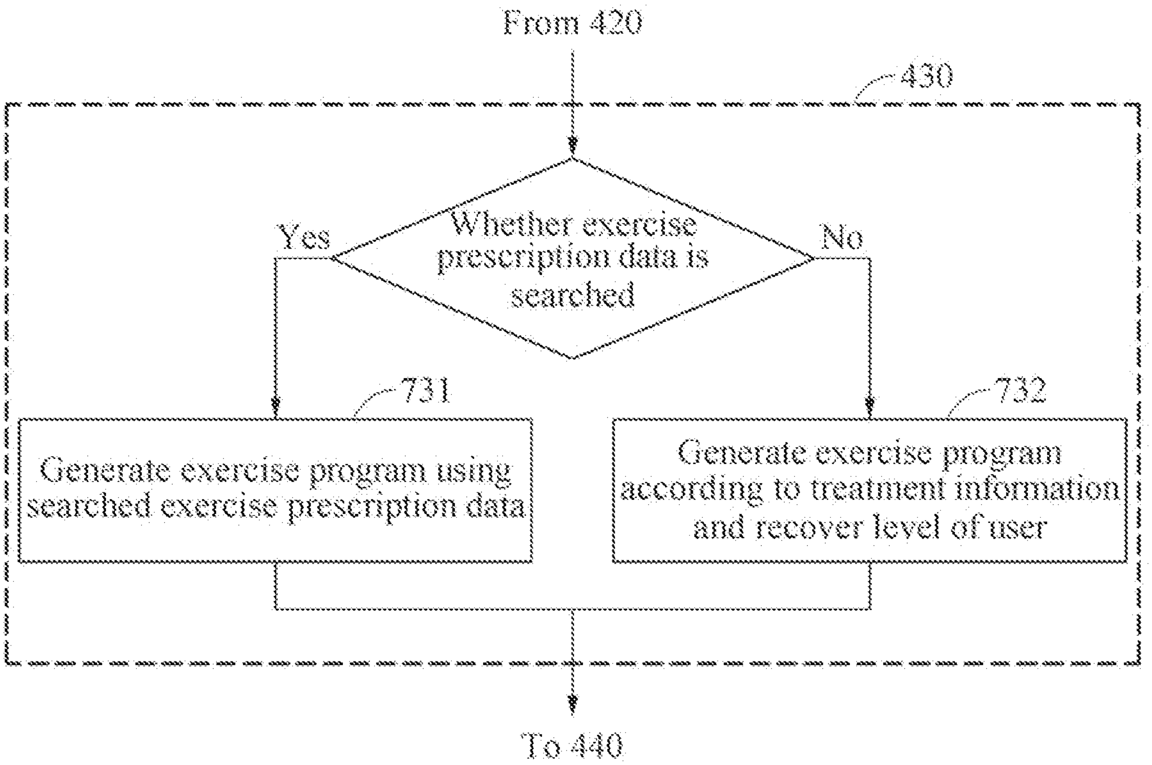
FIG. 7A is a flowchart illustrating an operation in which an electronic device generates an exercise program using PHR data received from a server according to an embodiment.

FIG. 7A is a flowchart illustrating an operation in which an electronic device generates an exercise program using PHR data received from a server according to an embodiment.

In operation 731, in response to exercise prescription data being searched from PHR data received from a server, the electronic device (e.g., the electronic device 101 of FIG. 1 or the electronic device 200 of FIG. 2) may determine at least one or a combination of two or more of an exercise type, an exercise frequency, a target exercise intensity, and a target exercise time of an exercise program based on the searched exercise prescription data.

The exercise prescription data may include at least one of information on the exercise type, the exercise frequency, the target exercise time, and the target exercise intensity. The target exercise time may be an exercise time presented as a target to be achieved by the user. The target exercise intensity may be an exercise intensity presented as a target to be achieved by the user for the recovery of the user.

The exercise prescription data may further include information on an exercise type limit, an exercise time limit, an exercise intensity limit, and an HR limit. The exercise type limit may be an exercise type not allowed to the user. The exercise time limit may be a maximum exercise time allowed to the user while performing one time of exercise by the user. The exercise intensity limit may be a maximum exercise intensity allowed to the user to prevent injury. The HR limit may be a maximum HR that should not be exceeded during the exercise. The electronic device may generate an exercise program using various pieces of information included in the exercise prescription data.

In operation 732, in response to the exercise prescription data not being searched, the electronic device may generate an exercise program according to treatment information and a recover level. For example, in response to the exercise prescription data not being searched from the PHR data received from the server, the electronic device may determine at least one or a combination of two or more of the exercise type, the target exercise frequency, the target exercise time, or the target exercise intensity of the exercise program according to the treatment information and the recover level of the user. For example, when the exercise prescription data is not searched from the PHR data, the electronic device may extract the treatment information from the PHR data. The electronic device may identify a recovery target part of the user using the treatment information, and generate the exercise program using an exercise reference table corresponding to the recovery target part. The electronic device may extract the exercise information suitable for the user from the exercise reference table according to the recover level of the user, and generate the exercise program using the extracted exercise information.

Figure 7B:
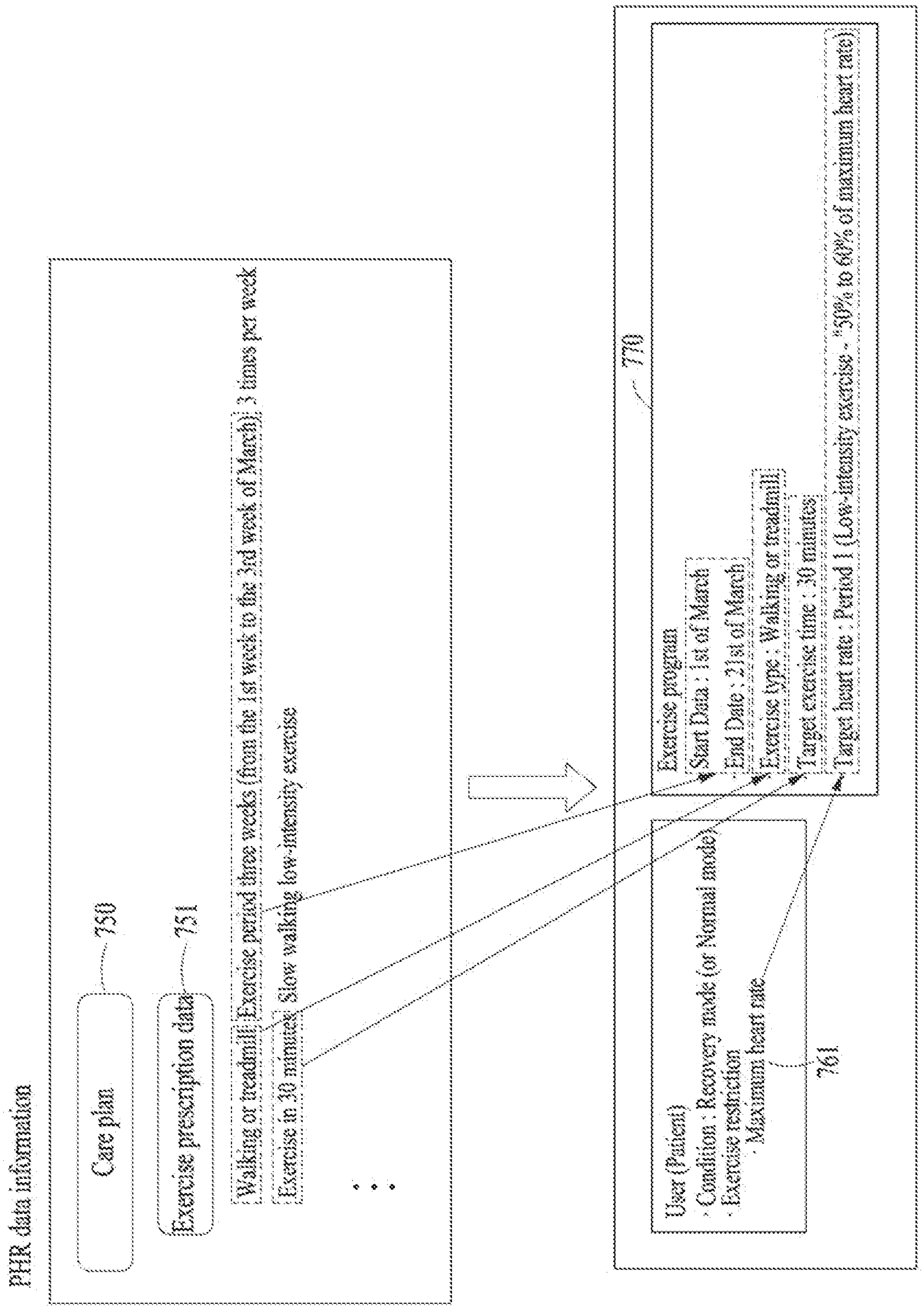
FIG. 7B illustrates a process in which an electronic device generates an exercise program using exercise prescription data included in PHR data according to an embodiment.

FIG. 7B illustrates a process in which an electronic device generates an exercise program using exercise prescription data included in PHR data according to an embodiment.

The PHR data received by the electronic device from the server may include a FHIR resource corresponding to a care plan 750. The care plan 750 may include exercise prescription data 751. Referring to FIG. 7B, the electronic device may set an exercise type of an exercise program 770 based on the exercise type such as walking or treadmill recorded in the exercise prescription data 751. The electronic device may set an exercise start date (e.g., 1st of March) and an exercise end date (e.g., 21st of March) of the exercise program 770 based on an exercise period (e.g., "from the 1st week to the 3rd week of March") recorded in the exercise prescription data 751. The electronic device may set a target exercise time (e.g., "30 minutes") of the exercise program 770 based on an exercise time (e.g., "exercise in 30 minutes") recorded in the exercise prescription data 751.

The electronic device may determine the target HR of the exercise program 770 using the maximum HR (HRmax) determined according to the age of the user. The maximum HR (HRmax) may refer to a maximum HR that may be stably increased through the exercise. For example, the maximum HR may be determined by Equation 1 shown in below.

$$\text{Maximum HR (HRmax)} = 200 - (\text{age of user}) \quad \text{Equation 1}$$

The exercise intensity may refer to calorie consumption per unit time. However, the exercise intensity is not necessarily limited thereto, and may be defined in other ways. The exercise intensity may be generally classified into low-intensity exercise, medium-intensity exercise, and high-intensity exercise, and the exercise intensity is related to the HR. For example, the low-intensity exercise may indicate an exercise intensity corresponding to the HR which is less than 64% of the maximum HR, the medium-intensity exercise may indicate an exercise intensity corresponding to the HR which is greater than or equal to 64% and less than 76% of the maximum HR, and the high-intensity exercise may indicate an exercise intensity corresponding to the HR which is greater than or equal to 76% of the maximum HR.

The electronic device may determine the age of the user from the PHR data, and calculate a maximum HR 761 of the corresponding user according to Equation 1. The electronic device may determine a target HR of the exercise program based on the exercise intensity (e.g., the "low-intensity exercise") recorded in the exercise prescription data 751 and the calculated maximum HR 761. For example, the electronic device may determine the target HR as an HR between 50% and 60% of the maximum HR.

In response to the exercise prescription data not being searched, the electronic device may generate the exercise program according to the treatment information and the recover level of the user. The electronic device may generate the exercise program based on the exercise reference table corresponding to a recovery target part.

For example, the electronic device may confirm that the user has undergone the heart valve replacement surgery during the surgical procedure based on the PHR data. Table 1 below shows the exercise reference table according to cardiac rehabilitation.

TABLE 1

| | |
|---|---|
| Acute phase | Walking with a cane or walker<br>3 to 5 times per week<br>Performing for 5 to 10 minutes |
| Subacute phase | Stretching, aerobic exercise using a bike or treadmill, light weight training<br>3 to 5 times per week<br>Performing for 15 to 20 minutes<br>Moderate intensity |
| Intensive outpatient therapy phase | Walking, stationary bike, calisthenics, light weight training<br>More than 3 times per week<br>Exercise intensity of 60% to 70% of maximum HR |
| Independent ongoing conditioning phase | Walking, stationary bike, calisthenics, light weight training<br>More than 3 times per week<br>Performing 60 minutes or longer<br>Exercise intensity of 70% to 80% of maximum HR |

The electronic device may extract the exercise information suitable for the user from the stored exercise reference table according to the recover level of the user. The electronic device may generate the exercise program by extracting the exercise information corresponding to a phase suitable for the health condition of the user from the exercise reference table according to the recover level of the user. For example, when the exercise program is generated immediately after the treatment of the user, the electronic device may determine that the user is in the acute phase. The electronic device may set the exercise type of the exercise program to "walking with a cane or walker", and may set the exercise frequency to 3 to 5 times per week. For the exercise information (e.g., the target exercise time or target exercise intensity) not recorded for the acute phase, the electronic device may determine the exercise information to be suitable for the user based on the treatment information of the PHR data and the recover level of the user.

In another example, the electronic device may confirm that the user has undergone shoulder joint surgery during the surgical procedure based on the PHR data. Table 2 below shows an exercise reference table according to shoulder joint rehabilitation.

TABLE 2

| | |
|---|---|
| Immediate postsurgical phase | Body and leg exercise, descending stairs, squats, lunges, trunk rotation exercise, thread the needle exercise<br>Performing 10 times per set, 3 sets a day |
| Intermediate phase | Bar exercise, abduction and adduction exercise, back extension exercise, internal rotation exercise, wall push exercise, side lying exercise, weight shifting exercise, lower trapezius exercise, low rowing exercise<br>Performing 10 times per set, 3 sets a day |
| Advance phase | Wall washing exercise, thread the needle exercise, punching exercise, lawn mowing exercise, threatening posture exercise<br>Performing 10 times per set, 3 sets a day |
| Strengthening exercise phase | Extension exercise, forward flexion exercise, internal rotation exercise, external rotation exercise, fist punch exercise, pull exercise<br>Performing 10 times per set, 3 sets a day |

In another example, the electronic device may confirm that the user has undergone knee surgery during the surgical procedure based on the PHR data. Table 3 below shows an exercise reference table according to knee rehabilitation.

TABLE 3

| | |
|---|---|
| First phase (3 weeks before surgery) | Active joint exercise (ankle pump exercise, straight leg lift, thigh strengthening exercise, plantar glide exercise, opposite leg knee flexion, knee flexion in a seated position)<br>Performing 20 times per session, 3 times a day |
| Second phase (after 3 weeks from surgery) | Closed kinetic chain training (CKC) exercise (calf lifting exercise, squatting exercise)<br>Performing 10 to 15 times per set, 3 sets a day |
| Third phase (after 4 weeks from surgery) | Functional training (forward lunge, heel lift exercise, stair descent exercise) |

Figure 8:
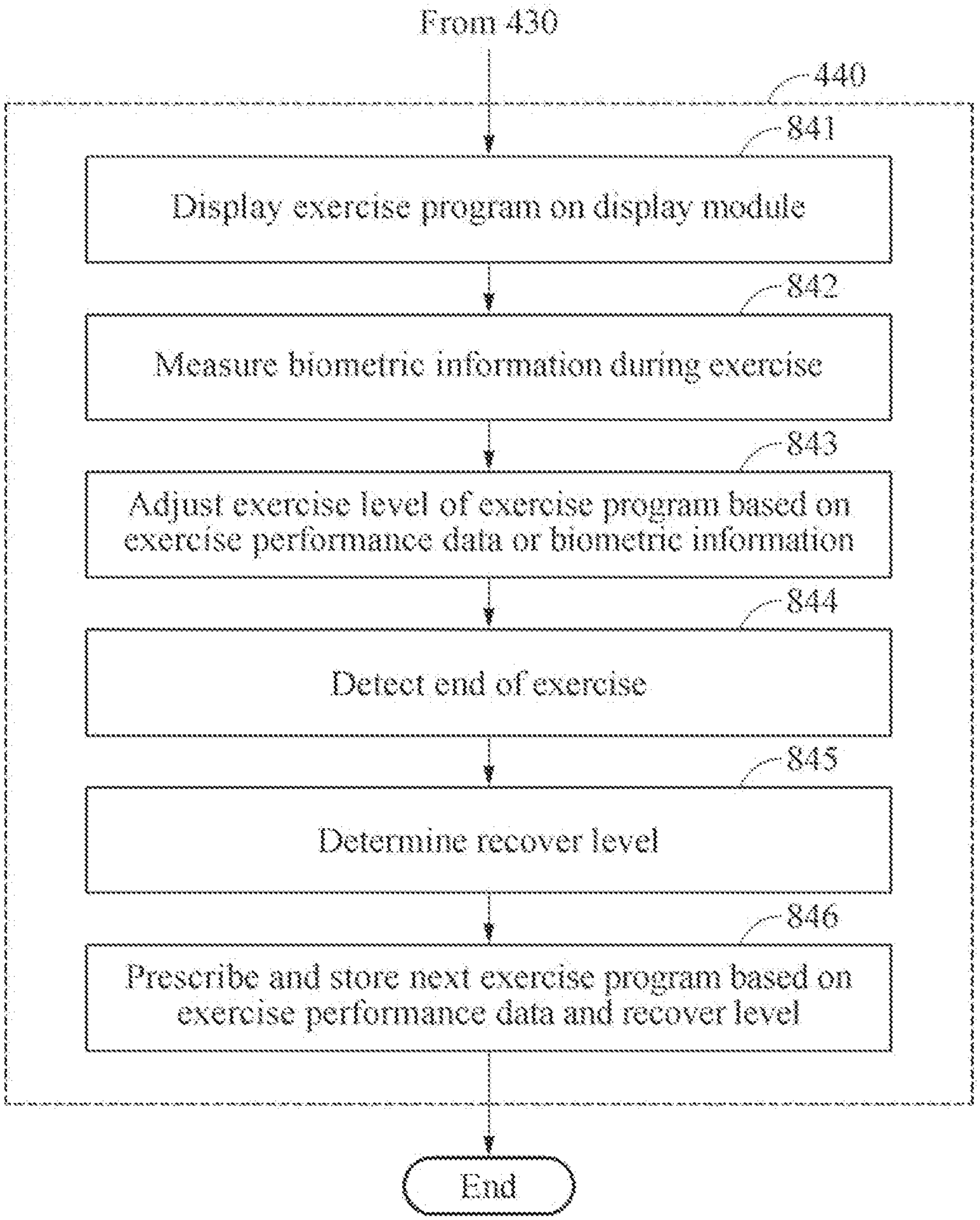
FIG. 8 is a flowchart illustrating an operation in which an electronic device provides feedback on an exercise program according to an embodiment.

FIG. 8 is a flowchart illustrating an operation in which an electronic device provides feedback on an exercise program according to an embodiment.

In operation 841, an electronic device (e.g., the electronic device 101 of FIG. 1 or the electronic device 200 of FIG. 2) may display an exercise program generated using PHR data on a display module (e.g., the display module 160 of FIG. 1 or the display module 220 of FIG. 2). The electronic device may display an exercise guide according to the exercise program on the display module. For example, when the electronic device detects that the user is exercising, the electronic device may display, on the display module, at least one of an exercise type, a target exercise frequency, a target exercise time, a target exercise intensity, and/or a target HR according to the generated exercise program. The electronic device may display, on a display, an exercise time limit and/or an HR limit according to the exercise program.

In operation 842, the electronic device may continuously measure the biosignal of the user, thereby obtaining biometric information when the user is exercising. For example, the electronic device may obtain SpO2 or the HR during the exercise of the user. The electronic device may obtain a stride during the exercise of the user using an acceleration sensor and a gyro sensor, and obtain a center of gravity balance during the exercise of the user using a pressure sensor. The electronic device may determine whether the exercise program generated from the PHR data is an exercise program suitable for the user, by using the biometric information (e.g., the SpO2, the HR) during the exercise of the user.

In operation 843, the electronic device may provide one of change or termination of the exercise program by adjusting an exercise level of the exercise program based on at least one of the exercise performance data or the biometric information during the exercise.

In response to a case where the exercise performance data of the user and the biometric information during the exercise reach a first threshold criterion, the electronic device may provide the change of the exercise program by increasing the exercise level of the exercise program. In response to a case where the exercise performance data of the user and the biometric information during the exercise reach a second threshold criterion, the electronic device may provide at least one of the change of the exercise program or the termination of the exercise program by lowering the exercise level of the exercise program.

When it is determined that the generated exercise program is not suitable for the user, the electronic device may adjust the exercise level of the exercise program. The electronic device may provide a more suitable exercise program to the user by adjusting the exercise level of the exercise program while the user is exercising. The exercise level may refer to a degree of load expected to be applied to the user's body. The exercise level may be determined based on the exercise type, the target exercise frequency, the target exercise time, the target exercise intensity, and the target HR of the exercise program.

Hereinafter, as examples of the first threshold criterion and the second threshold criterion, the number of times the exercise is stopped or the exercise intensity is reduced, or the detection of an abnormality of the biometric information of the user will be described. When it is confirmed that the user has not stopped the exercise or reduced the exercise intensity during a first number of times based on the exercise performance data after the execute level is changed, the electronic device may modify the exercise program by increasing the exercise level of the exercise program. When an abnormality is not detected in the biometric information of the user during the exercise for a predetermined period of time after the exercise level is changed, the electronic device may increase the exercise level of the exercise program. The electronic device may determine that there is an abnormality in the biometric information when the HR is significantly decreased, when the SpO2 is significantly low, or when the center of gravity balance is not maintained constantly. When the exercise level of the exercise program is increased, the electronic device may increase the exercise intensity of the exercise program, increase the target exercise time, increase the target exercise frequency, and increase the target HR. In another example, when it is confirmed that the user has stopped the exercise or reduced the exercise intensity a second number of times based on the exercise performance data after the exercise level of the exercise program is changed, the electronic device may modify the exercise program by lowering the exercise level of the exercise program. When the abnormality is detected in the biometric information of the user during the exercise after the exercise level of the exercise program is changed, the electronic device may lower the exercise level of the exercise program. However, the first threshold criterion and the second threshold criterion are not limited to the above example.

When a user's danger is detected using the exercise performance data and the biometric information during the exercise, the electronic device may output a warning message to the display module. When the user is exercising, if the exercise type of the exercise performed by the user does not match with the exercise type of the exercise program, the electronic device may output a warning message for the exercise type. When the exercise type of the exercise performed by the user is different from the exercise type of the exercise program, the electronic device may determine that the exercise types do not match with each other. When the user is exercising, if the exercise intensity of the exercise performed by the user exceeds the intensity limit, the electronic device may output a warning message for the exercise intensity. When the exercise time of the exercise performed by the user exceeds the time limit, the electronic device may output a warning message for the exercise time, and when the biometric information sensed for the user exceeds a biometric level limit, the electronic device may output a warning message for the biometric information on the display module.

In addition, when the exercise speed of the user goes beyond the target exercise speed of the exercise program and exceeds the exercise speed limit, the electronic device may output a warning message for the exercise speed on the display module. Furthermore, when the HR of the user goes beyond the target HR of the exercise program and an HR exceeding the HR limit is detected, the electronic device may determine that the user is in a dangerous state and output a warning message for the HR on the display module.

In operation 844, the electronic device may detect the end of the exercise of the user. In response to the detection of the end of the exercise of the user, the electronic device may display module an exercise performance result for the exercise program on the display module. The exercise performance result may indicate a result related to the extent to which the user has performed the exercise guide provided by the exercise program. For example, when the end of the exercise of the user is detected, the electronic device may calculate the exercise time of the user, and display information on the exercise time of the user compared to the target exercise time of the exercise program on the display module. In another example, the electronic device may calculate an average HR of the user during the exercise, and display information on the average HR of the user compared to the target HR of the exercise program on the display module. In another example, the electronic device may calculate a period of time in which the HR of the user during the exercise exceeds the HR limit of the exercise program, and display a total period of time during which the HR exceeds the HR limit on the display module.

In operation 845, the electronic device may determine a recover level after the end of the exercise of the user. The electronic device may determine the recover level using at least one or a combination of two or more of an increasing speed of the HR of the user during the exercise, exercise time, center of gravity balance information, SpO2 information, BP information, or HR recovery time after the exercise. Hereinafter, various methods of determining the recover level of the user will be described.

The electronic device may determine the recover level by comparing the biometric information during the exercise when the user is in the normal condition with the biometric information during the exercise when the user is in the rehabilitation condition. When the user is in the normal condition, the electronic device may pre-store the increasing speed of the HR, the exercise time, the center of gravity balance information, the SpO2 information, and the BP information during the exercise. When the user is in the rehabilitation condition, the electronic device may obtain the increasing speed of the HR, the exercise time, the center of gravity balance information, the SpO2 information, and the BP information during the exercise. For example, the electronic device may calculate the recover level by comparing the increasing speed of the HR when the user is in the normal condition with the increasing speed of the HR when the user is in the rehabilitation condition. In another example, the electronic device may calculate the recover level using the HR recovery time. The HR recovery time may be a period of time required for the HR to return to the normal level after the end of the exercise. The electronic device may determine the recover level by comparing the HR recovery time when the user is in the normal condition with the HR recovery time when the user is in the rehabilitation condition. In another example, the electronic device may calculate the recover level using HR reserve (HRR) representing a difference between a maximum HR and a resting HR. The electronic device may calculate the recover level by comparing the HRR when the user is in the normal condition with the HRR when the user is in the rehabilitation condition. In another example, the electronic device may calculate the recover level using the stride and the center of gravity balance information. The electronic device may calculate the recover level by comparing the stride and the center of gravity balance information when the user is in the normal condition with the stride and the center of gravity balance information when the user is in the rehabilitation condition. The electronic device may determine the recover level by calculating a similarity between the biometric information during the exercise in the rehabilitation condition and the biometric information during the exercise in the normal condition.

As described above, the electronic device may determine the recover level of the user in the rehabilitation condition by comparing the biometric information in the rehabilitation condition with the biometric information in the normal condition, however, the method of determining the recover level is not limited thereto. In a case of first exercise when the user is in the rehabilitation condition, the electronic device may determine the recover level by comparing with a case where the user is in the normal condition. In a case of the first exercise when the user is in the rehabilitation condition, the electronic device may determine the recover level by comparing with average data of others performing the rehabilitation having similar PHR data. When the user performs the exercise one or more times in the rehabilitation condition, the electronic device may also analyze how much better the user is than previous exercise in the rehabilitation condition. When the user is in the rehabilitation condition, the electronic device may determine the recover level by comparing biometric information during the previous exercise in the rehabilitation condition with biometric information during the current exercise in the rehabilitation condition. For example, the electronic device may calculate the recover level in consideration of the time required for the user to move a certain distance (e.g., 1 km) during the exercise. It is assumed that the user performs exercise of "walking". The electronic device may pre-store the time (e.g., 1 minute) required to move a distance of 1 km during the exercise of walking when the user is in the normal condition. The electronic device may calculate and store the time (for example, m minutes) required to move a distance of 1 km during the previous exercise in the rehabilitation condition. When it tasks n minutes to move a distance of 1 km during the current exercise in the rehabilitation condition, the electronic device may calculate the recover level by Equation 2 shown below. Herein, l, m, n are real numbers greater than or equal to 0.

$$\text{Recover level} = \frac{n-l}{m-l} \times 100(\%) \qquad \text{Equation 2}$$

In addition to this, when the user performs the exercise type in which the user may count the number of times of the exercise, the electronic device may also calculate the recover level based on the number of times the user performs the exercise per minute. After determining the recover level, the electronic device may end the measurement of the biosignal.

In operation 846, the electronic device may prescribe a next exercise program based on the exercise performance data and the recover level, and may store the next exercise program. The electronic device may generate an exercise program more suitable for the user based on the exercise performance result of the user for the autonomously provided exercise program. The electronic device may store the generated next exercise program and provide the stored next exercise program to the user when the user initiates the next exercise.

According to another embodiment, the electronic device may provide the exercise performance result and the exercise performance data of the user for the provided exercise program to a healthcare provider. For example, the electronic device may convert the exercise performance result and the exercise performance data of the user for the provided exercise program into data that may be provided as feedback, and transmit the converted data to a healthcare provider who previously prescribes the exercise to the user. The electronic device may receive feedback on the exercise program from the healthcare provider. The electronic device may receive, from the server, PHR data in which exercise prescription data newly prescribed by the healthcare provider is recorded. The electronic device may generate the next exercise program based on the new exercise prescription data recorded in the PHR data. When the user initiates the next exercise, the electronic device may provide the user with the generated next exercise program.

According to another embodiment, the electronic device may share the exercise performance result and the exercise performance data of the user for the provided exercise program with an external electronic device registered in the electronic device. For example, the electronic device may provide the exercise performance result of the user to external devices of family members and/or friends. The electronic device may transmit the exercise performance result of the user to the server. The electronic device may receive feedback on the exercise performance result from external electronic devices of family members and/or friends. For example, the electronic device may transmit the exercise performance result of the user to an external electronic device registered as a guardian of the user of the electronic device through the server. The external electronic device registered as a guardian may monitor the electronic device based on the received data.

The electronic device may provide a notification through an external electronic device operatively connected to the electronic device. For example, the electronic device may provide a notification through an external electronic device connected through short-range communication (e.g., Wi-fi or Bluetooth) in an Internet of Things (IoT) environment. The electronic device may provide the notification through an external electronic device connected to the same account within the server.

Figure 9:
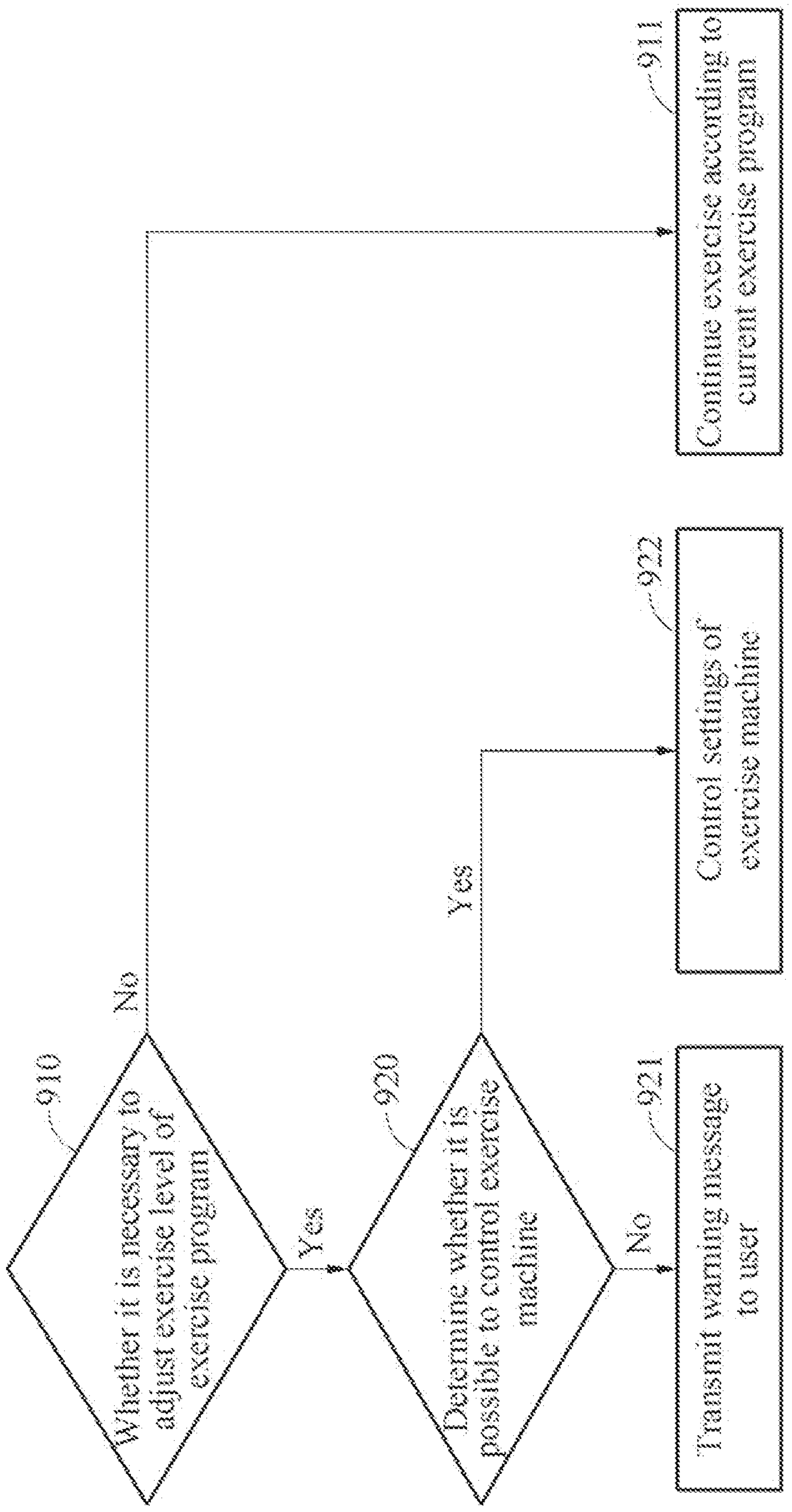
FIG. 9 is a flowchart illustrating an operation in which an electronic device transmits an instruction to an exercise machine based on an exercise program generated from PHR data according to an embodiment.

FIG. 9 is a flowchart illustrating an operation in which an electronic device transmits an instruction to an exercise machine based on an exercise program generated from PHR data according to an embodiment.

A communication module (e.g., the communication module 190 of FIG. 1) of an electronic device (e.g., the electronic device 101 of FIG. 1 or the electronic device 200 of FIG. 2) may establish communication with an exercise machine. A processor (e.g., the processor 120 of FIG. 1) of the electronic device may be configured to instruct the exercise machine to perform at least one or a combination of two or more of exercise start, exercise intensity control, exercise termination, and warning instruction of the exercise machine based on the exercise program generated from the PHR data.

In operation 910, when the user is exercising, the electronic device may determine whether it is necessary to adjust the exercise level of the exercise program based on at least one of the exercise performance data or the biometric information of the user during the exercise. When it is determined that the exercise program is not suitable for the user, the electronic device may adjust the exercise level of the exercise program. As described above, in response to a case where the exercise performance data of the user and the biometric information during the exercise reach the first threshold criterion, the electronic device may modify the exercise program by increasing the exercise level of the exercise program. In addition, in response to a case where the exercise performance data of the user and the biometric information during the exercise reach the second threshold criterion, the electronic device may modify the exercise program by lowering the exercise level of the exercise program or end the exercise program.

In operation 911, in a response to a case where it is not necessary to adjust the exercise level of the exercise program, the electronic device may not modify the exercise program. The electronic device may allow the user to continuously exercise according to the provided exercise program. The electronic device may not transmit a separate instruction to the exercise machine. The electronic device may transmit an instruction to maintain the current exercise program to the exercise machine.

In operation 920, when it is necessary to adjust the exercise level of the exercise program, the electronic device may determine whether it is possible to control an exercise machine for which communication is established. For example, when the user is exercising using an exercise device such as a treadmill, the electronic device may determine whether it is possible to control the settings of the treadmill. The electronic device may determine whether the exercise machine is controlled in a process of establishing the communication with the exercise machine before operation 910. In this case, operation 920 may be omitted, or only an operation of confirming whether it is possible to control the exercise machine based on the above determination may be performed.

In operation 921, when the electronic device may not control the exercise machine for which communication is established, the electronic device may transmit a warning message to the user. The electronic device may transmit a warning signal to the exercise machine so that the exercise machine outputs a warning message, or the electronic device may transmit the warning signal directly to the user using at least one of a display module, a sound, or tactile sense.

In operation 922, when the electronic device may control the exercise machine for which communication is established, the electronic device may control the settings of the exercise machine according to the modified exercise program. The electronic device may control the settings of the exercise machine to allow the user to perform exercise with a low exercise intensity or exercise with a high exercise intensity according to a changed exercise program. For example, when the user is exercising using a treadmill exercise machine, the electronic device may control a speed of the treadmill according to an exercise speed of the modified exercise program. In another example, the electronic device may control an operation time of the treadmill according to a target exercise time of the modified exercise program.

The invention claimed is:

1. An electronic device comprising:

a communication interface;

at least one processor electrically connected to the communication interface; and a memory electrically connected to the at least one processor, wherein the at least one processor is configured to:

receive medical data of a user from a server;

determine whether the user is in a rehabilitation condition based on the received medical data;

when the user is determined to be in the rehabilitation condition, generate a first exercise program corresponding to a recovery target part of the user using the received medical data;

display the generated first exercise program on the electronic device;

during the rehabilitation condition, increase monitoring of biometric information of the user by increasing at least two types of sensors, included in the electronic device, activated for measurement of the biometric information during the first exercise program performed by the user when compared to a condition in which recovery is not needed, the sensors comprising:

a green light emitting diode (LED) configured to measure a heart rate of the user, the green LED configured to contact the user's skin;

a red LED configured to measure the heart rate of the user based on light emitted by the red LED penetrating the user's skin;

an infrared (IR) LED configured to measure the heart rate and a saturation pulse oxygen of the user; and a pressure sensor configured to measure a center of gravity balance of the user;

based on the activated measurement of the biometric information of the user of the sensors, detect an abnormality of the biometric information that comprises:

when at least one LED of the green LED, the red LED, or the IR LED is activated, detecting the abnormality of the biometric information, based on the heart rate of the user has decreased;

when the IR LED is activated, detecting the abnormality of the biometric information, based on the saturation pulse oxygen of the user has decreased; and when the pressure sensor is activated, detecting the abnormality of the biometric information, based on the center of gravity balance of the user is not maintained;

when the abnormality of the biometric information is detected during the first exercise program, transmit, by the electronic device, an instruction without human intervention, to decrease at least one of a speed or an operation time of the exercise machine;

when the abnormality of the biometric information is not detected during the first exercise program, transmit, by the electronic device, an instruction without human intervention to increase at least one of the speed or the operation time of the exercise machine;

after end of the first exercise program, determine recovery level of the user based on comparison of biometric information of the user obtained during the first exercise program based on increasing the at least two types of sensors used and biometric information of the user during the condition in which recovery is not needed;

generate a second exercise program following the first exercise program based on the recovery level of the user without human intervention; and display the second exercise program.

2. The electronic device of claim 1, wherein the at least one processor being configured to determine whether the user is in the rehabilitation condition includes being configured to:

extract treatment information from the received medical data; and in response to determining that a current time point is before an expected recovery time of the user from a treatment start time point has elapsed, determine that the user is in the rehabilitation condition, the expected recovery time of the user being based on the treatment information.

3. The electronic device of claim 1, wherein the at least one processor being configured to display the first exercise program corresponding to the recovery target part of the user includes being configured to:

in response to exercise prescription data being searched from the received medical data, determine at least one or a combination of two or more of an exercise identification, a target exercise frequency, a target exercise time, or a target exercise intensity of the first exercise program based on the searched exercise prescription data; and in response to the exercise prescription data not being searched from the received medical data, determine at least one or a combination of two or more of the exercise identification, the target exercise frequency, the target exercise time, or the target exercise intensity of the first exercise program according to treatment information and the recovery level of the user.

4. The electronic device of claim 1, wherein the at least one processor is further configured to:

while the user is determined to be in a normal condition, obtain biometric information of the user in a first cycle; and while the user is determined to be in the rehabilitation condition, obtain the biometric information of the user in a second cycle which is shorter than the first cycle.

5. The electronic device of claim 1, wherein the at least one processor is further configured to:

while the user is determined to be in a normal condition, determine whether the user is exercising based on a first exercise condition; and while the user is determined to be in the rehabilitation condition, determine whether the user is exercising based on a second exercise condition that is different than the first exercise condition.

6. The electronic device of claim 1, wherein the at least one processor being configured to provide feedback on the first exercise program includes being configured to:

when the user is determined to be exercising, provide one of change or termination of the first exercise program by adjusting an exercise level of the first exercise program based on at least one of exercise performance data or the biometric information of the user during the exercising.

7. The electronic device of claim 1, wherein the at least one processor is further configured to:

determine the recovery level using at least one or a combination of two or more of an increasing speed of a heart rate (HR) of the user when the user is exercising, an exercise duration, center of gravity balance information, saturation of percutaneous oxygen (SpO2) information, blood pressure (BP) information, and HR recovery time after the exercising.

8. The electronic device of claim 1, wherein the at least one processor being configured to provide feedback on the first exercise program includes being configured to:

when the user is exercising, in response to at least one of determining that the exercising performed by the user does not match with an exercise identification of the first exercise program, determining that an exercise intensity of the exercising performed by the user exceeds an intensity limit, determining that an exercise duration of the exercising performed by the user exceeds a duration limit, or determining that biometric information sensed for the user exceeds a biometric level limit, output a warning message to a display module.

9. The electronic device of claim 1, wherein the communication interface is further configured to establish communication with the exercise machine, and wherein the at least one processor is further configured to instruct the exercise machine to perform at least one or a combination of two or more of exercise start, exercise intensity control, exercise termination, and warning instruction of the exercise machine based on the first exercise program.

10. The electronic device of claim 1, wherein the communication interface is further configured to establish communication with the exercise machine operable according to the first exercise program, and wherein the at least one processor is further configured to when the user is determined to be exercising:

adjust an exercise level of the first exercise program based on at least one of the exercise performance data or the biometric information of the user during the first exercise program, and transmit, to the exercise machine, an instruction indicating at least one of a decrease in an exercise intensity or exercise termination of the exercise machine.

11. A method performed by an electronic device, the method comprising:

receiving, by the electronic device, medical data of a user from a server;

determining, by the electronic device, whether the user is in a rehabilitation condition based on the medical data of the user received from the server;

when the user is determined to be in the rehabilitation condition, generating, by the electronic device, a first exercise program corresponding to a recovery target part of the user using the received medical data;

displaying, by the electronic device, the generated first exercise program on the electronic device;

during the rehabilitation condition, increase monitoring, by the electronic device, of biometric information of the user by increasing at least two types of sensors, included in the electronic device, activated for measurement of the biometric information during the first exercise program performed by the user when compared to a condition in which recovery is not needed, the sensors comprising:

a green light emitting diode (LED) configured to measure a heart rate of the user, the green LED configured to contact the user's skin;

a red LED configured to measure the heart rate of the user based on light emitted by the red LED penetrating the user's skin;

an infrared (IR) LED configured to measure the heart rate and a saturation pulse oxygen of the user; and a pressure sensor configured to measure a center of gravity balance of the user;

based on the activated measurement of the biometric information of the user of the sensors, detecting an abnormality of the biometric information, the detection of the abnormality of the biometric information comprising:

when at least one LED of the green LED, the red LED, or the IR LED is activated, detecting the abnormality of the biometric information, based on the heart rate of the user has decreased;

when the IR LED is activated, detecting the abnormality of the biometric information, based on the saturation pulse oxygen of the user has decreased; and when the pressure sensor is activated, detecting the abnormality of the biometric information, based on the center of gravity balance of the user is not maintained;

when the abnormality of the biometric information is detected during the first exercise program, transmit, by the electronic device an instruction without human intervention to decrease at least one of a speed or an operation time of an exercise machine;

when the abnormality of the biometric information is not detected during the first exercise program, transmit, by the electronic device, an instruction without human intervention to increase at least one of the speed or the operation time of the exercise machine;

after end of the first exercise program, determining, by the electronic device, recovery level of the user based on comparison of biometric information of the user obtained during the first exercise program based on increasing the at least two types of sensors used and biometric information of the user during the condition in which recovery is not needed;

generating, by the electronic device, a second exercise program following the first exercise program based on the recovery level of the user without human intervention; and displaying, by the electronic device, the second exercise program.

12. The method of claim 11, wherein the determining whether the user is in the rehabilitation condition comprises:

extracting treatment information from the received medical data; and in response to determining that a current time point is before an expected recovery time of the user from a treatment start time point has elapsed, determining that the user is in the rehabilitation condition, the expected recovery time of the user being based on the treatment information.

13. The method of claim 11, wherein the displaying the first exercise program corresponding to the recovery target part of the user comprises:

in response to exercise prescription data being searched from the received medical data, determining at least one or a combination of two or more of an exercise identification, a target exercise frequency, a target exercise time, or a target exercise intensity of the first exercise program based on the searched exercise prescription data; and in response to the exercise prescription data not being searched from the received medical data, determining at least one or a combination of two or more of the exercise identification, the target exercise frequency, the target exercise time, or the target exercise intensity of the first exercise program according to treatment information and the recovery level of the user.

14. The method of claim 11, further comprising:

while the user is determined to be in a normal condition, obtaining biometric information of the user in a first cycle, and determining whether the user is exercising based on a first exercise condition; and while the user is determined to be in the rehabilitation condition, obtaining the biometric information of the user in a second cycle which is shorter than the first cycle, and determining whether the user is exercising based on a second exercise condition different from the first exercise condition.

15. The method of claim 11, further comprises providing feedback on the first exercise program comprising:

when the user is determined to be exercising, providing one of change or termination of the first exercise program by adjusting an exercise level of the first exercise program based on at least one of the exercise performance data or the biometric information of the user during the exercising.

16. The method of claim 11, further comprises providing feedback on the first exercise program comprises-comprising:

when the user is exercising, in response to at least one of determining that the exercising performed by the user does not match with an exercise identification of the first exercise program, determining that an exercise intensity of the exercising performed by the user exceeds an intensity limit, determining that an exercise duration of the exercising performed by the user exceeds a duration limit, or determining that biometric information sensed for the user exceeds a biometric level limit, outputting a warning message to a display module.

17. The method of claim 11, further comprising:

while the user is determined to be in a normal condition, determining whether the user is exercising based on a first exercise condition; and while the user is determined to be in the rehabilitation condition, determining whether the user is exercising based on a second exercise condition that is different than the first exercise condition.

18. The method of claim 11, further comprising:

determining the recovery level using at least one or a combination of two or more of an increasing speed of a heart rate (HR) of the user when the user is exercising, an exercise duration, center of gravity balance information, saturation of percutaneous oxygen (SpO2) information, blood pressure (BP) information, and HR recovery time after the exercising.

19. The method of claim 11, further comprising:

instructing the exercise machine to perform at least one or a combination of two or more of exercise start, exercise intensity control, exercise termination, and warning instruction of the exercise machine based on the first exercise program.

* * * * *